(12) United States Patent
McLaren et al.

(10) Patent No.: US 10,747,406 B2
(45) Date of Patent: Aug. 18, 2020

(54) UPDATING AN ELECTRONIC MEDICAL RECORD FOR A PATIENT

(71) Applicant: Medaxion, Inc., Nashville, TN (US)

(72) Inventors: Jeffrey Lee McLaren, Nashville, TN (US); William Dyer Rodes, II, Nashville, TN (US)

(73) Assignee: Medaxion, Inc., Nashville, TN (US)

( * ) Notice: Subject to any disclaimer, the term of this patent is extended or adjusted under 35 U.S.C. 154(b) by 340 days.

(21) Appl. No.: 15/803,529

(22) Filed: Nov. 3, 2017

(65) Prior Publication Data

US 2018/0059895 A1   Mar. 1, 2018

Related U.S. Application Data

(63) Continuation of application No. 13/708,725, filed on Dec. 7, 2012, now abandoned, and a continuation of
(Continued)

(51) Int. Cl.
| | |
|---|---|
| *G16H 10/60* | (2018.01) |
| *G06F 3/0484* | (2013.01) |
| *G06Q 50/24* | (2012.01) |
| *G06F 3/0485* | (2013.01) |
| *G06F 3/0488* | (2013.01) |

(52) U.S. Cl.
CPC .......... *G06F 3/0484* (2013.01); *G06F 3/0485* (2013.01); *G06F 3/04883* (2013.01); *G06Q 50/24* (2013.01); *G16H 10/60* (2018.01)

(58) Field of Classification Search
CPC ...................................................... G16H 10/60
See application file for complete search history.

(56) References Cited

U.S. PATENT DOCUMENTS

| | | |
|---|---|---|
| 6,322,502 B1 | 11/2001 | Schoenberg et al. |
| 7,542,911 B2 | 6/2009 | Barret et al. |

(Continued)

OTHER PUBLICATIONS

"Concerto Clinicals Whiteboard," *Concerto Clinicals*.
(Continued)

*Primary Examiner* — John A Pauls
(74) *Attorney, Agent, or Firm* — Baker Botts L.L.P.

(57) ABSTRACT

A method for updating an electronic medical record of a patient comprises retrieving, from a medical information management system, a patient monitoring worksheet displaying medical information relating to the delivery of medical care to a first patient and presenting, on a display capable of receiving touch-responsive user input, the retrieved patient monitoring worksheet. The method further comprises determining, for each subsection of the patient monitoring worksheet, whether information tracked during that subsection is incomplete. The method further comprises permitting edit popups only for the ones of the subsections with incomplete information in a first mode of operation and permitting edit popups for any of the subsections in a second mode of operation. The method further comprises detecting touch-screen input selecting a subsection with incomplete information, presenting an edit popup for the selected subsection, determining one or more added or edited values of the edit popup, and updating the patient monitoring worksheet by causing the one or more added or edited values to be stored by the medical information management system.

20 Claims, 8 Drawing Sheets

Related U.S. Application Data application No. 13/708,680, filed on Dec. 7, 2012, now abandoned.

(60) Provisional application No. 61/685,380, filed on Mar. 17, 2012, provisional application No. 61/630,372, filed on Dec. 9, 2011.

(56) References Cited

U.S. PATENT DOCUMENTS

| | | |
|---|---|---|
| 7,574,369 B1 | 8/2009 | Borza |
| 7,627,334 B2 | 12/2009 | Cohen et al. |
| 7,848,935 B2 | 12/2010 | Gotib et al. |
| 8,005,947 B2 | 8/2011 | Morris et al. |
| 2003/0069759 A1 | 4/2003 | Smith |
| 2005/0021369 A1 | 1/2005 | Cohen et al. |
| 2005/0033603 A1 | 2/2005 | Suzuki et al. |
| 2005/0055246 A1 | 3/2005 | Simon |
| 2006/0149589 A1 | 7/2006 | Wager |
| 2006/0195484 A1 | 8/2006 | Mahesh et al. |
| 2007/0073555 A1 | 3/2007 | Buist |
| 2007/0168223 A1 | 7/2007 | Fors et al. |
| 2007/0192133 A1 | 8/2007 | Morgan |
| 2007/0192137 A1 | 8/2007 | Ombrellaro |
| 2007/0233524 A1 | 10/2007 | Alban et al. |
| 2008/0154646 A1 | 6/2008 | Barrett et al. |
| 2008/0184360 A1 | 7/2008 | Kornilovsky et al. |
| 2009/0063189 A1 | 3/2009 | Hupke et al. |
| 2009/0241184 A1 | 9/2009 | Doering |
| 2010/0286997 A1 | 11/2010 | Srinivansan |
| 2010/0305970 A1 | 12/2010 | McLaren et al. |
| 2010/0305971 A1 | 12/2010 | McLaren et al. |
| 2010/0305972 A1 | 12/2010 | McLaren et al. |
| 2010/0305973 A1 | 12/2010 | McLaren et al. |
| 2010/0306858 A1 | 12/2010 | McLaren et al. |

OTHER PUBLICATIONS

Cormac Driver et al., "Facilitating Dynamic Schedules for Healthcare Professionals," © 2007, *IEEE*.

Elizabeth S. Chen et al., "PalmCIS: a Wireless Handheld Application for Satisfying Clinician Information Needs," *Journal of the American Medical Information Association*, vol. 11, No. 1, Jan./Feb. 2004.

Marcela D. Rodriguez et al., "Location-Aware Access to Hospital Information and Services," *IEEE Transactions on Information Technology in Homemedicine*, vol. 8, No. 4, Dec. 2004.

"A&E Patient Monitoring System," *Blueberry Consultants*.

"Telergy Innovative Nurse Call Features for Healthcare Facilities," *GE Healthcare*, © 2009.

Eneida A. Mendonça et al, "Approach to Mobile Information and Communication for Health Care," *International Journal of Medical Information* (2004) 73, 631-638.

UPDATING AN ELECTRONIC MEDICAL RECORD FOR A PATIENT

RELATED APPLICATIONS

This application is a continuation of U.S. application Ser. No. 13/708,680 and U.S. application Ser. No. 13/708,725, both filed on Dec. 7, 2012 and both claim the benefit of U.S. Provisional Application No. 61/630,372 filed on Dec. 9, 2011.

TECHNICAL FIELD

The present disclosure relates generally to managing medical data, and more specifically to managing medical records and charts for one or more medical practices.

BACKGROUND

Medical professionals record, use and share medical records and charts for patients at various medical care establishments. For this purpose, medical professionals may use various physical files, written displays, and electronic systems. For example, many anesthesia care establishments use forms, charts, or other paperwork to track relevant information regarding patient care. For example, anesthesia professionals and other peri-operative service providers may use specially designed paper forms to document clinical data related to a surgical anesthesia case. Such documentation may be also used to record patient treatment events and generate corresponding invoices.

SUMMARY

In accordance with the present disclosure, a mobile electronic chart is provided which substantially eliminates or reduces disadvantages and problems associated with previous systems and methods.

According to a particular embodiment, a handheld apparatus for updating an electronic medical record for a patient comprises a display, a memory, a wireless network interface, and a processor. The display is capable of receiving touch-responsive user input, the memory maintains a medical information management application and the wireless network interface is capable of coupling to a medical information management system operable to maintain a plurality of patient monitoring worksheets. The processor is operable, when executing the medical information management application, to retrieve, from the medical information management system, a patient monitoring worksheet displaying medical information relating to the delivery of medical care to a first patient and present on the display the retrieved patient monitoring worksheet, the patient monitoring worksheet having a maximum viewable time range selected from the range of thirty minutes to four hours and equally divided into a plurality of time intervals, and wherein the patient monitoring worksheet comprises a plurality of simultaneously viewable display sections comprising a drugs display section, a fluids display section, a vital signs display section, and a physiological data display section; the drugs display section having a column listing a plurality of drugs and, for each of the drugs, a row capable of tracking of an amount of the drug administered for each of the time intervals, and wherein if a number of the drugs exceeds a drug list threshold, the drugs display section is vertically scrollable in response to touch-screen gesture control; the fluids display section having a column listing of a plurality of fluids and, for each of the fluids, a row capable of tracking of an amount of the fluid administered or expelled for each of the time intervals, and wherein if a number of the fluids exceeds a fluid list threshold, the fluids display section is vertically scrollable in response to touch-screen gesture control; the vital signs display section having a column indicating a scale and capable of tracking, for each of the equally distributed subintervals of time, a heart rate and a blood pressure of the patient charted on the scale; and the physiological data display section having a column listing a plurality of physiological data items and, for each of the physiological data items, a row capable of tracking a value for the physiological data item for each of the time intervals, and wherein if a number of the physiological data items exceeds a physiological data item list limit, the physiological data display section is vertically scrollable in response to touch-screen gesture control, wherein each of the time intervals of each of the display sections is a subsection. The processor is further operable, when executing the medical information management application, to detect a beginning of a new time interval, identify a first subsection configured to auto-populate a value, and auto-populate the first subsection with the first value upon determining a first value for the first subsection. The processor is further operable, when executing the medical information management application, to determine, for each subsection, whether information tracked during that subsection is incomplete and whether information corresponding to that subsection includes an auto-populated value, detect touch-screen input selecting a subsection with one or more of incomplete information or auto-populated values, and present, in a portion of the display, an edit popup for the selected subsection, an edit popup permitting one or more of editing or verification of values for information tracked in the subsection. The processor is further operable, when executing the medical information management application, to determine, based on user input, an edited or verified value for the selected subsection and update the patient monitoring worksheet for the first patient by causing the edited or verified value to be stored by the medical information management system.

According to another embodiment, a method for updating an electronic medical record of a patient comprises retrieving, from a medical information management system, a patient monitoring worksheet displaying medical information relating to the delivery of medical care to a first patient, the medical information management system operable to maintain a plurality of patient monitoring worksheets. The method further comprises presenting, on a display capable of receiving touch-responsive user input, the retrieved patient monitoring worksheet displaying medical information relating to the delivery of medical care to a patient, the patient monitoring worksheet having a maximum viewable time range selected from the range of thirty minutes to four hours and equally divided into a plurality of time intervals, and wherein the patient monitoring worksheet comprises a plurality of simultaneously viewable display sections comprising a drugs display section, a fluids display section, a vital signs display section, and a physiological data display section; the drugs display section having a column listing a plurality of drugs and, for each of the drugs, a row capable of tracking of an amount of the drug administered for each of the time intervals, and wherein if a number of the drugs exceeds a drug list threshold, the drugs display section is vertically scrollable in response to touch-screen gesture control; the fluids display section having a column listing of a plurality of fluids and, for each of the fluids, a row capable of tracking of an amount of the fluid administered or expelled for each of the time intervals, and wherein if a number of the fluids exceeds a fluid list threshold, the fluids display section is vertically scrollable in response to touch-screen gesture control; the vital signs display section having a column indicating a scale and capable of tracking, for each of the equally distributed subintervals of time, a heart rate and a blood pressure of the patient charted on the scale; and the physiological data display section having a column listing a plurality of physiological data items and, for each of the physiological data items, a row capable of tracking a value for the physiological data item for each of the time intervals, and wherein if a number of the physiological data items exceeds a physiological data item list limit, the physiological data display section is vertically scrollable in response to touch-screen gesture control, wherein each of the time intervals of each of the display sections is a subsection. The method further comprises determining, for each subsection, whether information tracked during that subsection is incomplete. The method further comprises permitting edit popups only for the ones of the subsections with incomplete information in a first mode of operation and permitting edit popups for any of the subsections in a second mode of operation, wherein toggling between the first mode of operation and the second mode of operation is based on user input. The method further comprises detecting touch-screen input selecting a subsection with incomplete information and presenting, in a portion of the display, an edit popup for the selected subsection, an edit popup permitting one or more of adding or editing of information tracked in the subsection, the information tracked in the subsection comprising one or more values. The method further comprises determining, based on user input, one or more added or edited values of the edit popup and updating the patient monitoring worksheet for the first patient by causing the one or more added or edited values to be stored by the medical information management system.

According to yet another embodiment, a system for updating an electronic medical record for a patient comprises a central medical information management system and one or more medical information management applications. The central medical information management system is operable to maintain a plurality of patient monitoring worksheets that correspond to patients associated with a medical practice at a practice location during a predetermined period of time. The one or more medical information management applications each reside on a wireless handheld device and are operable, when executed, to present, on a display capable of receiving touch-responsive user input, a patient monitoring worksheet displaying medical information relating to the delivery of medical care to a first patient, the patient monitoring worksheet having a maximum viewable time range selected from the range of thirty minutes to four hours and equally divided into a plurality of time intervals, and wherein the patient monitoring worksheet comprises a plurality of simultaneously viewable display sections comprising a drugs display section, a fluids display section, a vital signs display section, and a physiological data display section; the drugs display section having a column listing a plurality of drugs and, for each of the drugs, a row capable of tracking of an amount of the drug administered for each of the time intervals, and wherein if a number of the drugs exceeds a drug list threshold, the drugs display section is vertically scrollable in response to touch-screen gesture control; the fluids display section having a column listing of a plurality of fluids and, for each of the fluids, a row capable of tracking of an amount of the fluid administered or expelled for each of the time intervals, and wherein if a number of the fluids exceeds a fluid list threshold, the fluids display section is vertically scrollable in response to touch-screen gesture control; the vital signs display section having a column indicating a scale and capable of tracking, for each of the equally distributed subintervals of time, a heart rate and a blood pressure of the patient charted on the scale; and the physiological data display section having a column listing a plurality of physiological data items and, for each of the physiological data items, a row capable of tracking a value for the physiological data item for each of the time intervals, and wherein if a number of the physiological data items exceeds a physiological data item list limit, the physiological data display section is vertically scrollable in response to touch-screen gesture control, wherein each of the time intervals of each of the display sections is a subsection. The one or more medical information management applications are further operable, when executed, to detect a beginning of a new time interval, identify a first subsection configured to auto-populate a value, and auto-populate the first subsection with the first value upon determining a first value for the first subsection. The one or more medical information management applications are further operable, when executed, to determine, for each subsection, whether information tracked during that subsection is incomplete. The one or more medical information management applications are further operable, when executed, to permit edit popups only for the ones of the subsections with incomplete information in a first mode of operation and permit edit popups for any of the subsections, wherein toggling between the first mode of operation and the second mode of operation is based on user input in a second mode of operation. The one or more medical information management applications are further operable, when executed, to update the patient monitoring worksheet for the first patient by causing the first value to be stored by the medical information management system.

Another technical advantage realized by at least some embodiments of the present disclosure is the ability to present, on a display of limited size, a synthesized version of complex medical information related to patient care. By providing an improved interface of this kind, the amount of visual work and effort needed to locate relevant and/or pertinent patient care information is reduced relative to prior art interfaces such as those provided by electronic automated anesthesia record keeping systems. As an example, an embodiment of the present disclosure provides a medical chart interface comprising a subset of medical data available for a particular patient (e.g., data regarding one or more of drug administration, fluid administration, medical events, monitored physiologic data, and laboratory data) that is organized in a manner that allows for simultaneous viewing of the subset of information without having to navigate to another interface. Such embodiment enables visual focus on medical chart data despite the size constraints of displays such as hand held devices. In one or more such embodiments, the improved interface further allows for user interaction with the subset of data (e.g., enabling adding or editing of data) without navigating away to another interface. As will be described in more detail herein, in some embodiments, the subset of data is selected for presentation according to a maximum viewable time range.

Particular embodiments provide various technical advantages. These techniques facilitate the charting of medical information related to patient care or physiological events as they occur. For example, anesthesia professionals or other peri-operative service providers may record vital signs measurements, drug administrations, fluid administrations/output measurements, case milestone time recording, time-based annotations, physiologic monitor values measurements, laboratory values measurements, care provider attendance, case involvement timeframes, medical history, surgical diagnosis, surgical procedures, anesthetic procedures, patient conditions, drug allergies, and patient identifying information. In particular embodiments, the system may receive physiologic monitored values, vital signs and other data electronically from equipment in the operating room. Certain embodiments may provide seamless rapid entry of patient related data such that active patient care is not interrupted during a medical procedure. In this regard, indications of incomplete data may be provided for later completion by the user. Charted medical information can be viewed concurrently by multiple users and may also be used in generating medical care invoices.

Particular embodiments provide alerts to notify users of the presence of incomplete data. Such techniques may include notifying a user about incomplete data on a predetermined notification schedule defined for the practice. In this manner, a medical practice may ensure that patient care related information is completed by the user in close time proximity to the medical care events thereby limiting inaccuracies in data values.

Particular embodiments use templates. Templates may define the default drugs, fluids, events, vital signs, monitored physiological data, and laboratory information available to a user. Templates may be specific to a practice or a procedure and can be modified as needed by an administrator. In certain embodiments, templates may also provide common values for the recorded data. Templates may also define the list of additional drugs, fluids, vital signs, monitored physiological data, or laboratory information that may be added by the user as needed during a particular case.

Other technical advantages of the present invention will be readily apparent to one skilled in the art from the following figures, descriptions, and claims. Moreover, while specific advantages have been enumerated above, various embodiments may include all, some, or none of the enumerated advantages.

DESCRIPTION OF EXAMPLE EMBODIMENTS

Figure 1:
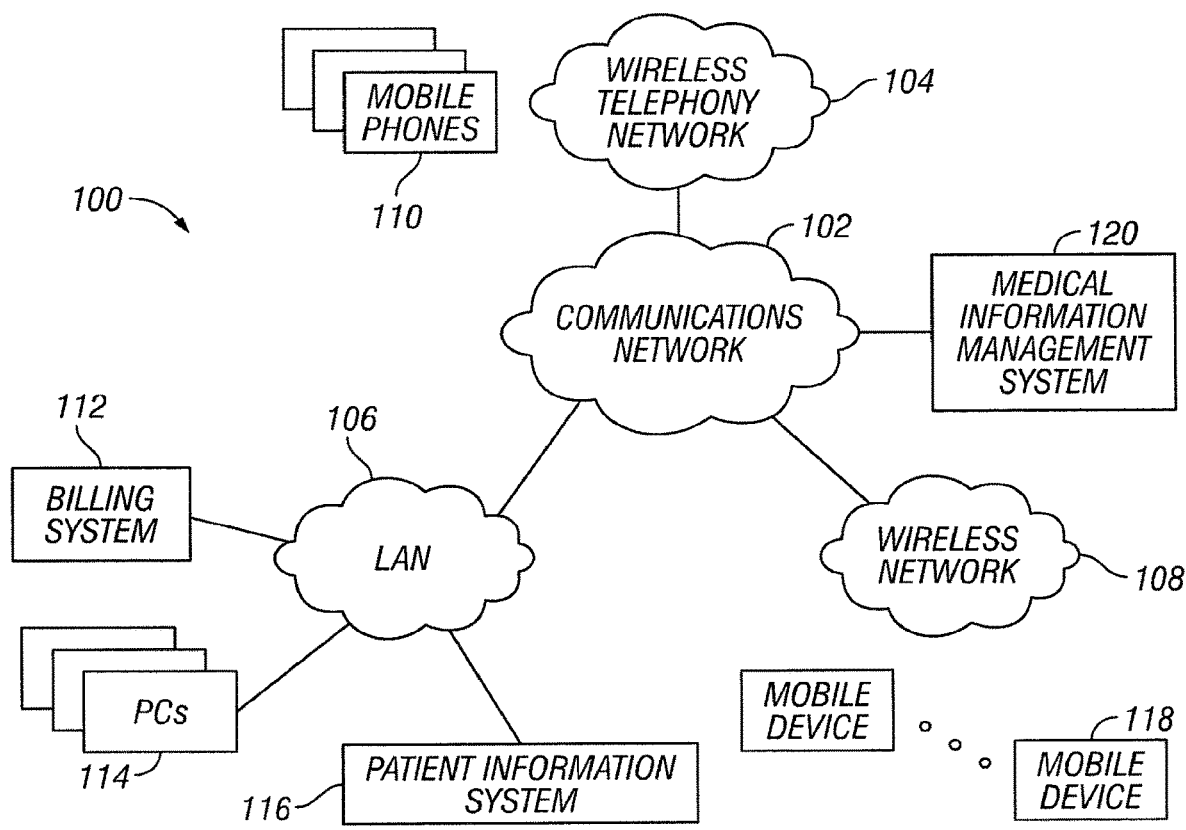
FIG. 1 is a block diagram illustrating a system environment with elements that interoperate to manage and display medical case information including medical chart information.

FIG. 1 is a block diagram illustrating a system 100 with elements that interoperate to manage and display medical case information. The elements of system 100 can support a number of different operations, including maintaining a central, unified repository of patient and case information for one or more practices, facilitating maintenance and display of a graphical electronic medical chart, enabling entry and display of drugs, fluids, events, vital signs, physiological data, and laboratory information regarding the patient, facilitating presentation and alerting of incomplete data in conjunction with particular patient treatment episodes, and providing an intuitive graphical user interface for interacting with the system. Systems and methods of maintaining, recording, and displaying an electronic medical chart according to this disclosure may be provided in conjunction with the medical case management techniques disclosed in U.S. patent application Ser. Nos. 12/789,783; 12/789,858; 12/789,900; 12/789,962; and Ser. No. 12/790,011, the disclosures of which are incorporated herein by reference.

Medical professionals can use the medical information and functionality of system 100 to manage one or more cases for a particular medical practice with one or more practice locations. Users of system 100 can include medical professionals and associated staff, such as surgeons, anesthesiologists, other physicians, certified registered nurse anesthetists (CRNAs), hospital management, billing personnel, medical record managers, and any other medical staff. Under appropriate circumstances, system 100 may further provide patients access to selected information. According to particular embodiments, system 100 may be used to manage information for one or more medical practices. A medical practice is any organization of associated medical professionals and associated personnel, such as a group of doctors and support staff with a common specialty that potentially practice at one or more different practice locations, a group of doctors and support staff associated with a particular hospital, or any other suitable organization of medical professionals. For example, an anesthesia practice may include anesthesiologists, CRNAs, and other support staff that practice at a set of particular medical treatment facilities.

In the illustrated embodiment, system 100 includes a number of elements interconnected by various networks, including a communications network 102, a wireless telephony network 104, a local area network 106, and a wireless network 108. Networks 102, 104, 106, and 108 represent communications equipment, including hardware and any appropriate controlling logic, for interconnecting elements and facilitating communication between these elements. Communications network 102 may include local area networks (LANs), metropolitan area networks (MANs), wide area networks (WANs), any other public or private network, local, regional, or global communication network, enterprise intranet, other suitable wireline or wireless communication link, or any combination thereof. Communications network 102 may include any combination of gateways, routers, hubs, switches, access points, base stations, and any other hardware, software, or a combination of the preceding that may implement any suitable protocol. For illustrative purposes, system 100 is also shown as including other specific types of networks, including wireless telephony network 104, local area network 106, and wireless network 108. The use of these or similar networks facilitate seamless communication between components of system 100 regardless of their geographic location or communication protocols.

As illustrated, system 100 includes a wireless telephony network 104 coupled to communications network 102. Wireless telephony network 104 represents communications equipment, including hardware and any appropriate controlling logic, for interconnecting elements and facilitating communications by wireless devices. Wireless telephony network 104 may include gateways, call managers, routers, hubs, switches, access points, base stations, cellular towers, radio networks, satellite telephone equipment implementing appropriate protocols for wireless telephony communications. While only one wireless telephony network 104 has been illustrated, it should be understood that various embodiments may operate using more than one wireless telephony network. In addition, various embodiments may incorporate wireless telephony networks 104 in other networks of system 100 such as, for example, wireless network 108.

The illustrated embodiment of system 100 also includes a local area network 106 coupled to communications network 102. Local area network 106 represents communications equipment, including hardware and any appropriate controlling logic, for interconnecting elements within a limited network area (as compared with, for example, wide area networks). Local area network 106 may include any combination of gateways, routers, hubs, switches, access points, base stations, and any other hardware, software or combination thereof using suitable protocols to support communications. For example, local area network 106 may be the established network infrastructure deployed at a particular hospital or other medical facility. While only one local area network 106 has been illustrated, it should be understood that various embodiments may operate using multiple local area networks 106. In addition, various embodiments may incorporate local area networks 106 in other networks of system 100.

System 100 also includes wireless network 108 coupled to communications network 102. Wireless network 108 represents communications equipment, including hardware and any appropriate controlling logic, for wirelessly interconnecting elements and facilitating communication between other elements of system 100. For example, wireless network 108 may operate according to one or more of the 802.11 standards promulgated by the Institute of Electrical and Electronic Engineers (IEEE). Wireless network 108 may include any combination of gateways, routers, hubs, switches, access points, base stations, wireless telephone systems and any other hardware, software, or combination thereof. While only one wireless network 108 has been illustrated, it should be understood that various embodiments may operate using multiple wireless networks 108. In addition, various embodiments may incorporate wireless networks 108 in other networks of communications network 102.

These networks interconnect other elements of system 100, including mobile phones 110, a billing system 112, personal computers (PCs) 114, patient information system 116, mobile devices 118, and a medical information management system 120. It should be understood that while system 100 is illustrated as including specific types of networks, various embodiments may operate using any suitable arrangement and collection of networks that enable appropriate communications.

Mobile phones 110 represent portable hardware and appropriate controlling logic for providing telephony and/or advanced data services. For example, mobile phones 110 may support voice and data communications. Mobile phones 110 may include smart phones capable of transmitting and receiving multiple forms of media including but not limited to still audio, text messages, video, images, and content from disparate services. As illustrated, mobile phones 110 may be coupled to wireless telephony network 104 and capable of communicating to other components of system 100. According to particular embodiments, system 100 may use mobile phones to provide alerts or other information to medical personnel.

Billing system 112 represents hardware, appropriate controlling logic, and data associated with billing for medical services. For example, billing system 112 may be a computer server designed to manage billing for a particular medical practice, such as an anesthesia practice. Billing system 112 may be network accessible to facilitate communication with other elements of system 100.

Personal computers (PCs) 114 represent general-purpose computers, including appropriate hardware, controlling logic, and data that may be used to interface with other system components such as billing system 112, patient information system 116, mobile devices 118, and medical information management system 120. For example, PCs 114 may be workstations, laptops, netbooks, tablet computers, personal data assistants (PDAs), or any other suitable computing device. PCs 114 may support a wide variety of operations such as web browsing, word processing, and managing business data. According to particular embodiments, PCs 114 provide access, potentially through web-based interfaces, to information managed by other elements.

Patient information system 116 represents suitable hardware components, controlling logic, and data for managing patient information, such as patient demographic information, medical histories, medical charts, laboratory information and/or other relevant medical information such as practice employees and work schedules. For instance, patient information system 116 may be embodied in a computer system or a network of computers, which are capable of maintaining patient information such as patient identifiers, case identifiers, surgery types, date-of-birth, surgery schedule, operating room, attending surgeon and/or anesthesiologist, insurance information, medical history, medical charts and laboratory information corresponding to particular procedures and other patient-specific information as appropriate for various aspects of a medical practice. Some embodiments of the present disclosure may include a patient information system 116 deployed at a medical practice or other medical care facility, while other embodiments may include a global patient information system 116 for maintaining patient information. As illustrated, patient information system 116 may be coupled to a network, such as local area network 106, to facilitate communication to other elements of system 100. While only one patient information system 116 is shown, it should be understood that various embodiments may include multiple appropriately deployed patient information systems 116.

As will be recognized by one of ordinary skill in the art, mobile devices such as smart phones and tablets have limited screen real estate available for visualizing concepts since data controls are larger (for touch-ability) and screen sizes are smaller (for portability) than traditional computer screen presentations. Accordingly, a challenge for displaying and inputting medical data on mobile devices is organizing the data, within a single interface, in a manner that also permits the entry of data. Indeed, because the screen size is limited, there is not enough space to visually present all medical data available for one or more patients, let alone have that data be finger-selectable, without disorienting view changes in scale.

Mobile devices 118 represent any suitable portable hardware, including appropriate controlling logic and data, capable of communicating with remote devices to facilitate management of medical information. For example, mobile devices 118 may include, but are not necessarily limited to, mobile telephones, advanced ("smart") phones, personal digital assistants (PDAs), wireless handsets, notebook computer systems, and tablet computer systems. According to particular embodiments, mobile devices 118 include wireless devices with advanced user interfaces, such as the APPLE iPhone, iPod Touch, or iPad.

Medical information management system 120 represents any appropriate combination of hardware, controlling logic, and data for managing medical information and supporting interactive access to that data from multiple remote (and potentially highly mobile) devices. For example, medical information management system 120 may include a networked server or collection of networked servers, or could include in one or more virtual servers capable of acquiring computing resources on-demand depending on the dynamically determined needs of the system. Using virtual servers, medical information management system 120 could be scaled dynamically based on system requirements and real-time usage, without limiting operation to a particular physical computer server having fixed computing resources. This could facilitate the scalability, efficient operation, high availability, and cost effectiveness of the system. As illustrated, medical information management system 120 couples to networks, such as communications network 102, to facilitate communication to other elements of system 100.

Particular embodiments are designed to operate in a network environment that facilitates the retrieval and presentation of medical data to end users, facilitating real-time tracking of medical professional activity related to the provision of patient care (events tracked at or near in time to the actual provision of patient care) provided at a medical facility such as a hospital or other medical care establishment. Systems, methods, and software exemplified in the present disclosure may increase the coordination of patient care, enhance the reliability of medical information, and help ensure the accuracy of medical record keeping and billing.

In operation, elements of system 100 operate together to perform various medical information management functions including but not limited to maintaining a central, unified repository of patient and case information for one or more practices, facilitating maintenance and display of a graphical electronic medical chart, enabling entry and display of drugs, fluids, events, vital signs, physiological data, and laboratory information regarding the patient, facilitating presentation and alerting of incomplete data in conjunction with particular patient treatment episodes, and providing an intuitive graphical user interface for interacting with the system.

For example, medical information management system 120 is capable of maintaining a central, unified repository of electronic medical chart information corresponding to a various medical procedures for numerous patients of one or more medical practices. In particular embodiments, the medical chart information may be presented in an electronic patient monitoring worksheet having various sections to facilitate the tracking of various categories of medical information. Medical information management system 120 may maintain the drugs, fluids, events, vital signs, physiological data, and laboratory information related to a patient and enable users to dynamically track and record data values corresponding to these categories for patients of one or more medical practices. Medical information management system 120 can dynamically update this information based on communications with medical personnel using mobile devices 118 (or other suitable access devices). Medical information management system 120 may also access and exchange information with other information management and processing elements of system 100. In particular embodiments, medical information management system 120 acquires patient management information from one or more patient information systems 116. For example, medical information management system 120 can upload patient information for all patients scheduled for treatment on a particular day. Medical information management system 120 may also include configurable templates for medical charts based on practice location or the particular medical procedure to be performed by the patient. Thus, for example, the default choices for drugs, fluids, events, vital signs, physiological data, and laboratory information may be determined based on such templates.

Medical information management system 120 maintains information on patients and medical professional activity and supports interactions with other devices to manage and display the medical and logistics information. For instance, mobile devices 118 can access medical information management system 120 to download information for display in the form of a graphical electronic medical chart for the selected patient of a particular practice location. In certain implementations, mobile devices 118 may present the electronic medical chart information in a particular tab of a tabbed interface where each tab provides information related to a patient's treatment. Mobile devices 118 could further interface with medical information management system 120 to receive and manage more detailed patient treatment information through other specialized interfaces, such as a case summary interface for summarizing information for a case or a case details interface for detailing the chronology and other medical events associated with a case. For example, mobile devices 118 may present a graphical user interface showing patient treatment records in tabbed interfaces with the ability to list medical events for real-time tracking of cases, and provide medical case chart information in a separate tab. Users of mobile devices 118 can use these interfaces to provide real-time entry of information corresponding to treatment events including medical charting, which medical information management system 120 can then use to update the case board and medical chart. This type of process uses the capture of treatment information (such as billable events or other required records) to feed other processes that, in typical systems, require separate efforts to track, such as paper forms or charts that may be error prone or lack the safeguards related to incomplete data as provided by the present disclosure.

Particular embodiments support secure access to medical information management system 120 using an access scheme designed to maintain a high level of security while supporting user-friendly access with devices that may have limited or non-traditional user interfaces. The access techniques may use a combination of authorization information checked in one or more steps, such as a username, password, quick access code (such as a personal identification number (PIN) or other string of characters or gestures), secure hash, device identifiers, or other secure authentication information. In certain embodiments, secure authentication is a multi-step process that uses different types of information provided at different stages of access. According to particular embodiments, one step may involve device identification. For example, a particular mobile device 118 may have a secure device hash or other suitable unique identifier that can be registered with and verified by medical information management system 120. Another step may involve a secure token or key that uniquely maps to a particular medical practice (which may use information from other steps, such as a secure device hash that links a specific mobile device 118 to a particular medical practice). Another step may involve providing a user name and associated password, for example, by selecting a user name from a list of available users and then providing a password that meets certain length and character requirements. Another step may require entry of a quick access code, such as a four or six number pin or a particular pre-recorded gesture. These different steps and secure authentication information may be combined and used at particular times to ensure that access to medical information is suitably restricted while allowing authorized users of mobile devices 118 relatively easy access to information. For example, after requiring one or more relatively high-security authentication steps, subsequent access over the course of some period of time may only require a subset of credentials, such as a quick access code. During that period of time, mobile device 118 could enter sleep modes or other application and, upon a user wishing to restart access to medical information, mobile device 118 would simply require reentry of the quick access code. If mobile device 118 were restarted or some extended period of time passed, system 100 could require reprocessing through one or more of the higher security steps.

After access is granted, the user may select a practice location from a list of available practice locations for the medical practice and thereby gain access to the corresponding medical case information and functionality of the system. Following authentication, mobile devices 118 and medical information management system 120 may interoperate to present medical information, including medical chart information, in an intuitive graphical case board interface to the user. For example, the electronic medical chart may enable the entry and display of drugs, fluids, events, vital signs, physiological data, and laboratory information regarding the patient, facilitate presentation and alerting of incomplete data in conjunction with particular patient treatment episodes, and provide an intuitive graphical user interface for interacting with the system.

The graphical user interface allows medical professional activity, case board information, medical charts, and patient treatment records to be securely accessed and displayed. In addition, this information can be used to track billing-related events as a patient progresses through various medical events or sub-events of a particular surgery or other medical procedure. For example, mobile devices 118 may securely present a medical chart to understand the treatment the patient is undertaking during a medical procedure, where medical information management system 120 actually maintains all of this information. Similarly, PCs 114 may securely access medical information management system 120 to view similar information. Thus, for instance, an interface available at PCs 114 may display patient information or medical events maintained by medical information management system 120, portions of which may be indirectly derived from other components of system 100 such as patient information system 116 or one or more mobile devices 118.

System 100 may further provide incomplete data alerting functionality that enables targeted messaging to appropriate medical professionals using a variety of communication techniques and protocols. Incomplete data alerts may occur automatically by the system based on configurable notification templates and notify users of the presence of incomplete data that requires user attention. Additionally, alerts may take on a variety of forms including voice, text, multimedia, or application specific (e.g., embedded notification in a customer medical information management application running on mobile devices 118). In the case of automatic notifications, alerting schemes may deliver alerts or notifications on the occurrence of some predefined case event or on a predefined interval after a patient treatment episode has been completed. As discussed later in this disclosure, appropriate indicators of incomplete data may be displayed using suitable color schemes, shading, or shapes. Incomplete data alerts can be sent to a variety of individuals and can based on various roles including medical case role, team management role, or context-based role such as those who respond to specific clinical changes. Incomplete data alerts may also be delivered on disparate networks. For example, medical information management system 120 may deliver an alert message or notification via communications network 102 and wireless telephony network 104 to mobile phones 110. Thus, medical professionals may be notified of incomplete data in the form of voice, text, or multimedia messages even after leaving the associated medical facility.

Elements of system 100 may also facilitate coordination with a billing system 112 to develop invoices and reports. For example, medical information management system 120 may communicate with one or more billing systems 112 to support billing-related functions. Thus, medical information management system 120 can support billing systems 112 to produce appropriate invoices for surgical procedures, anesthesia services and/or other billing-related medical events corresponding to a medical provider site (e.g., a particular hospital or hospital floor) or individual patients. Billing system 112 may then forward invoices or other billing information to the appropriate insurance provider, patient, or other responsible party. Thus, a billing system may be seamlessly integrated with other functionality described in this disclosure to perform various medical billing operations.

While system 100 is illustrated as including specific components arranged in a particular configuration, it should be understood that various embodiments may operate using any suitable arrangement and collection of components capable of providing functionality such as that described.

Figure 2:
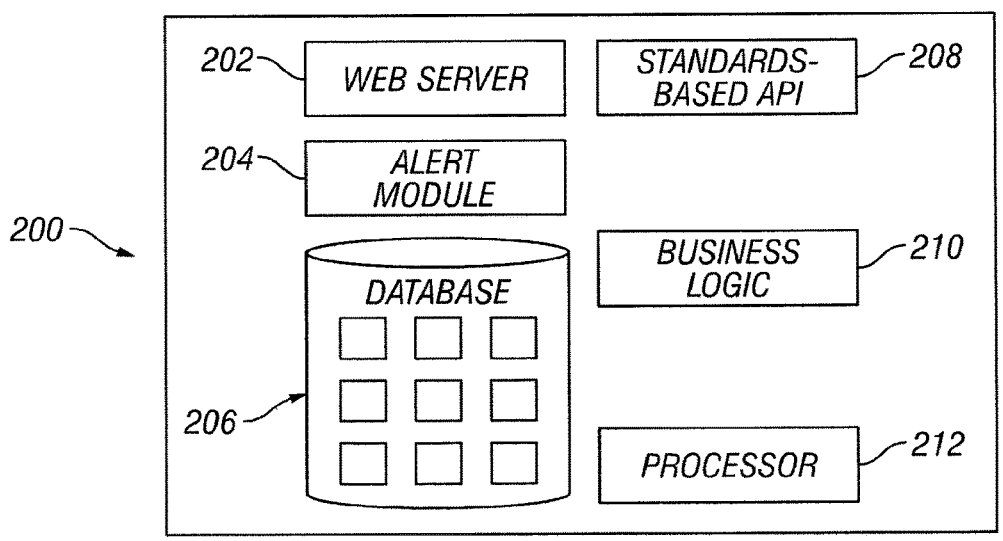
FIG. 2 is a block diagram illustrating an example medical information management system for facilitating management of medical case information including medical chart information.

FIG. 2 is a block diagram illustrating a system 200 representing an example embodiment of medical information management system 120 which has elements that interoperate to facilitate the management of medical chart information. The elements of system 200 can support a number of different operations including maintaining a central unified repository of patient and case information for one or more practices, which permits the maintenance of medical chart information. The elements of system 200 may also facilitate incomplete data alerting in conjunction with tracked medical cases and the graphical display of a user interface for interacting with the system and the entry of medical chart information from one or more devices such as mobile phones 110, PCs 114, and mobile devices 118.

System 200 represents any appropriate combination of hardware, controlling logic, and data. For example, system 200 may be one or more computer servers or virtual computer servers capable of providing the appropriate functionality for centrally managing patient and case information for one or more practices. As illustrated, system 200 includes a web server 200, an alert module 204, a database 206, a standards-based application programming interface (API) 208, business logic 210, and one or more processors 212.

Web server 202 represents any appropriate combination of hardware, controlling logic and data for interfacing with remote devices using web-based protocols to provide web-based access to the medical information and functionality provided by system 200. For example, web server 202 may be a web host that serves web pages to facilitate access to some or all functions of system 200.

Alert module 204 represents any appropriate combination of hardware, controlling logic, and data for facilitating incomplete data alerting in conjunction with tracked medical cases and activities of a medical care team. In addition, alert module 204 may be coupled to one or more networks such as a telephone network, a wired or wireless computer networks, a cellular network, a radio network, a satellite network, or any other appropriate network capable of delivering alerts.

Database 206 represents any appropriate combination of hardware, controlling logic, and data for maintaining patient information, case information, medical chart information, medical professional activity information, and other system-related data. As illustrated, database 206 has various data components including patient data, case data, medical chart data, user data, practice data, templates, system metadata, location data, device registry data, user access logs, and rules data.

Patient data includes information regarding patients tracked by system 200. For example, for each patient tracked by system 200, database 206 may maintain a patient identifier (such as a name), general demographic information (such as the patient's date-of-birth), and any appropriate responsible party or insurance information.

Case data represents a collection of information corresponding to a particular case associated with a scheduled medical procedure for a patient at a defined medical facility. Such information may include a case identifier or reference, information on a procedure scheduled to occur or currently occurring (such as surgery type), an assigned operating room, the attending physician or anesthesiologist, records of the case chronology of a scheduled medical procedure, various medical events in the case chronology, involvement by specific medical professionals, medical chart information, procedure and diagnostic codes, modifiers, and audit logs corresponding to various medical events entered by specific practice personnel. According to particular embodiments, system 200 updates case data based on real-time inputs from mobile devices 118. System 200 can provide patient treatment records to other devices based on information maintained in patient and case data.

User data represents a collection of information corresponding to various users who interact with system 200, including users of PCs 114, mobile phones 110, and mobile devices 118. Such user information may include authentication data such as authorized users corresponding to a defined practice location, each authorized user's passwords, each authorized user's system access history, each authorized user's usage preferences, and other access codes. This information can be used to provide secure access to system 200 and as appropriate, prohibit unauthorized access to medical information maintained by system 200.

Practice data represents practice wide settings and preferences corresponding to a medical practice and, potentially, for one or more specific practice locations. This may include rules and policies for managing medical data instituted by a particular medical practice. Practice data may also include a core set or subset of medical procedure terminology for a medical practice or procedure. Such medical procedure terminology may conform to Current Procedural Terminology (CPT) or International Classification of Diseases (ICD) codes. Such codes may be used in conjunction with recording billing-related events for a particular practice. Practice data may also include information related to historic utilization and appropriate future allocation of medical professional resources available to the practice. Other information included in practice data may include billing report preferences, billing export preferences, and any translation or transmission settings necessary to communicate various reports to the defined medical practice at a particular location. This information facilitates the generation of billing reports and invoices in the desired format for a practice.

Location data includes information corresponding to a defined practice location, either tied to a particular medical practice at that location or based on rules of information about multiple medical practices that may provide care at that location. Location data may include case chronology templates, medical chart templates, checklist templates, quality control templates (such as a physician quality reporting incentives (PQRI) template), and other templates for capturing information in a form customized to a particular practice location or practice location/medical practice specified manner. These templates facilitate the recording of medical chart information, medical events occurring in the field, and real-time tracking of quality control measures. For example, a case chronology template may define a set of rules regarding entry of medical events associated with a procedure and include time events or other entries. Templates may be modified and updated by a web-based administrative capability.

Rules data defines permitted or prohibited activities corresponding generally to users, medical professional roles, specific medical practices, locations, medical procedures, or other activities. For example, these rules may implement practice-specific or location-specific policies affecting medical professionals or relevant medical events. For example, a rule for an anesthesia practice may prohibit an anesthesiologist from managing more than four CRNAs. Thus these rules provide guidelines for active case management in terms of a workflow that can be specific to a medical specialty or a medical facility.

Standards-based API 208 represents hardware, appropriate controlling logic, and data for interfacing with remote components using standardized processes and protocols. For example, standards-based API 208 may interface with patient information systems 116 to retrieve patient information from one or more medical practices. As another example, standards-based API 208 may facilitate interactions with remote devices to support alerting functions, such as through text messaging with mobile phones 110.

Business logic 210 represents hardware, controlling logic and data associated that controls the fundamental operation and administration of system 200, including interactions of elements to provide the interactive medical information management processes described herein. For example, business logic 210 may be software for execution by one or more processors to provide a central medical information management service that tracks medical professional activity, medical chart information, and various other aspects of patient care, and interfaces with mobile devices 118. Processor 212 represents one or more computer processors for executing business logic 210 or other software or controlling logic associated with elements of system 200.

In operation, elements of system 200 operate together to perform various functions of the present disclosure, including maintaining a central, unified repository of patient data, case information, and medical chart information for one or more practices and facilitating the maintenance of medical professional activity information, patient treatment information including case chronology, medical chart information, and medical case summary information. System 200 uses this information to support applications on mobile devices 118 that can interface with and graphically present that information. In addition, system 200 facilitates alerting for tracked medical cases including providing notifications of incomplete data. Elements of system 200 can ensure that users of system 200 are securely authenticated prior to accessing medical information, medical chart information, and case management functions. Accordingly, only those users who are properly authenticated may interact with system 200.

For example, elements of system 200 are operable to maintain a central, unified repository of patient information, medical chart information, and case information for one or more medical practices. In particular, processors 212 may execute appropriate business logic 210 to communicate with one or more patient information systems 116 to retrieve patient information corresponding to a medical practice. System 200 stores information in database 206, generates day-of-care information (for example, based on patient information retrieved from one or more patient information systems 116), communicates information from database 206 to computing devices (e.g. mobile phones 110, PCs 114, and/or mobile devices 118), and receives updates, including real-time information, from one or more computing devices. This information can then be used by a graphical user interface to display and facilitate real-time data entry and management of medical case and chronology information. Any changes occurring at these computing devices that are relevant to real-time case management including medical chart information, and medical professional coordination may then be received over a network. Accordingly, elements of system 200 interact with one another to actively manage medical case information as patients receive care.

As discussed above, system 200 may impose various authentication requirements before permitting access to functions and information of system 200. These may include one or more levels of interactive authentication steps requiring user interactions as well as ongoing, automated exchanges. For example, each communication or request from a particular mobile device 118 may include a secure device hash identifying that mobile device 118 to system 200.

According to particular embodiments, system 200 implements a multi-level access scheme that requires different types of credentials at each level. For example, system 200 could require a user name and password (potentially in combination with a device hash) for first-level access and then a quick access code for second level access and for re-access over some period of time. System 200 may compare these received values with stored user data according to business logic 210 to determine whether the user identified in the request has appropriate credentials for accessing the medical information and functionality of system 200. Using these secure authentication means, system 200 can guarantee that access to case information and specific patient medical data is appropriately protected.

During operation, system 200 provides medical information, such as case board, medical professional activity, or patient treatment information, for presentation and use by graphical user interfaces presented on mobile devices 118. To support this functionality, system 200 maintains real-time tracking information for patients receiving care, and activities of identified medical professionals, provides the information to mobile devices 118, and receives and processes requests to update the information. For responding to medical case board and medical chart information requests, medical data for multiple cases and charts may be accessed for retrieving a subset of the details for forwarding to the remote computing device to display on its graphical user interface. For example, in response to a medical chart request from mobile device 118, system 200 may compile selected information for a particular patient scheduled to or receiving care at a practice location for a medical practice associated with the requesting mobile device 118 and then provide that information to the requesting mobile device 118, for example, in a graphical electronic medical chart.

Mobile devices 118 may also request information or provide updates for particular cases or medical charts. In response, system 200 may provide responsive patient treatment records that include details of the requested patient including medical chart information extracted from database 206 (potentially with more information than for case board requests). The accessed case data may include medical professional activity data relative to the case, procedure information, diagnosis information, medical chart information, case chronology data such as medical events associated with a particular case and any related checklist items. As appropriate, system 200 may log requests or other access events in the access logs of database 206 according to business logic 210 and any corresponding rules maintained in the rules data of database 206.

In responding to information requests, system 200 may process the response information as appropriate based on the requesting computing device. Such processing may include formatting the case board, patient treatment record, or medical chart according to location data in database 206. For example, medical chart information may be arranged according to a template that may organize and populate sections of a medical chart according to templates in the location data for a specific practice. For an anesthesia or other appropriate practice those predefined sections may correspond to drugs, fluids, events, vital signs, physiological data, and laboratory information. Thus, the templates and other information in the location data of database 206 instruct processor 212 and business logic 210 how a practice wishes the requested information to be populated, organized, and delivered for subsequent presentation on a graphical user interface of a requesting computing device. However, some or all of the customization and formatting of information may be handled by other elements, such as mobile devices 118.

In addition to facilitating the display of chronological stages at one or more remote computing devices, system 200 can also receive real-time updates corresponding to specific billing-related events such as the performance of a step in a medical procedure. According to particular embodiments, some or all of these may be "real-time," that is, provided from care-givers as (or very nearly in time to) a patient receiving care indicated by an update. For example, an anesthesiologist may use mobile device 118 to track, in real-time, time spent with a patient or time spent actually administering anesthesia from start to finish. Such durational information may be provided to system 200 and maintained in an appropriate time record of a patient treatment record or an appropriate medical chart record. Updates may also include specific events from the medical chart, or policy-based requirements of a medical procedure. Once an update is processed, other computing devices may securely receive case information including these updates in the form of case board information, medical chart information, patient treatment records, an alert, or other appropriate form. In this manner, all medical professionals associated with the case can be kept aware of any changes occurring in real-time for a particular case.

During operation, system 200 may also provide alerting functionality to notify medical professionals of relevant medical events, incomplete data, or other concerns. According to particular design considerations, alerts may be automatically generated or user-initiated. For automatic alerts, system 200 is operable to maintain a list of customizable events for which a alert should be issued. For example, notifications of incomplete data may be sent out as alerts according to customized policies regarding treatment of incomplete data. Such policies may be practice or procedure specific. In particular, database 206 may include a set of alert rules specifying alerts, rules for triggering an alert (such as occurrence of a particular event or a certain period of time after completion of a patient treatment episode), and alert execution information (such as contact information and procedures for handling a triggered alert). Subsequent events, such as updates to case data or presence of incomplete data can then trigger alerts. For example, a medical establishment may have a policy that incomplete data related to vital signs be addressed within 15 minutes after a patient treatment episode or logout of the system in order to ensure data accuracy and completeness.

Alert module 204 may send an alert messages using any appropriate formats and protocols, including voice, text, or multimedia messages, based on the targeted device. As discussed, the form and network for delivering an alert may be defined by the contact information of the event trigger. For example, the contact information may indicate that a supervising medical professional wishes to be notified of relevant incomplete data fields in the form of a text message using a short message service (SMS) network. In certain implementations, alert system 204 may support interactive alerts. For example, in addition to notifying particular medical professionals of incomplete data, alert module 204 may facilitate the completion of incomplete data by providing an interface for allowing medical professionals to enter appropriate values in the medical chart or other case interface. Accordingly, embodiments of the present disclosure support configuring, sending, and receiving automatic alerts for communicating medical events and incomplete data fields to medical professionals.

Alert module 204 can also process user-initiated messages. For example, a user of a particular mobile device 118 may choose to alert other users to a particular event or information. Once the case alert module 204 receives this user-initiated message, alert module 204 can determine how, when, and where to send the message based on the received message and intended recipient. In a similar manner, alert module 204 can also receive responses to user-initiated messages and forward them to the intended computing devices. User-initiated messages may be sent in any suitable form and using any appropriate network. For example, the messages may be a text, voice, or multimedia message sent over a wired, wireless, cellular, or any other network. Thus, system 200 allows medical professionals to stay apprised of real-time changes to case information and communicate with each other efficiently to assess the requirements of immediate patient care and coordinate effectively with each other.

System 200 may also interact with billing systems such as billing system 112 to develop billing invoices and reports. In particular, upon request or at defined intervals, system 200 may access practice data residing at database 206 that defines report preferences for delivery of billing-related events. In addition, system 200 may access export preferences, and translation and transmission settings for placing reports in appropriate form for delivery to the billing system 112 corresponding to a medical practice. Alternatively, export preferences may define the intended destination of bill reports or invoices. Thus, insurance companies and other responsible parties may receive a bill or an invoice developed according to their predefined report preferences.

While system 200 is illustrated as including specific components, it should be understood that various embodiments may operate using any suitable arrangement and collection of components.

Figure 3:
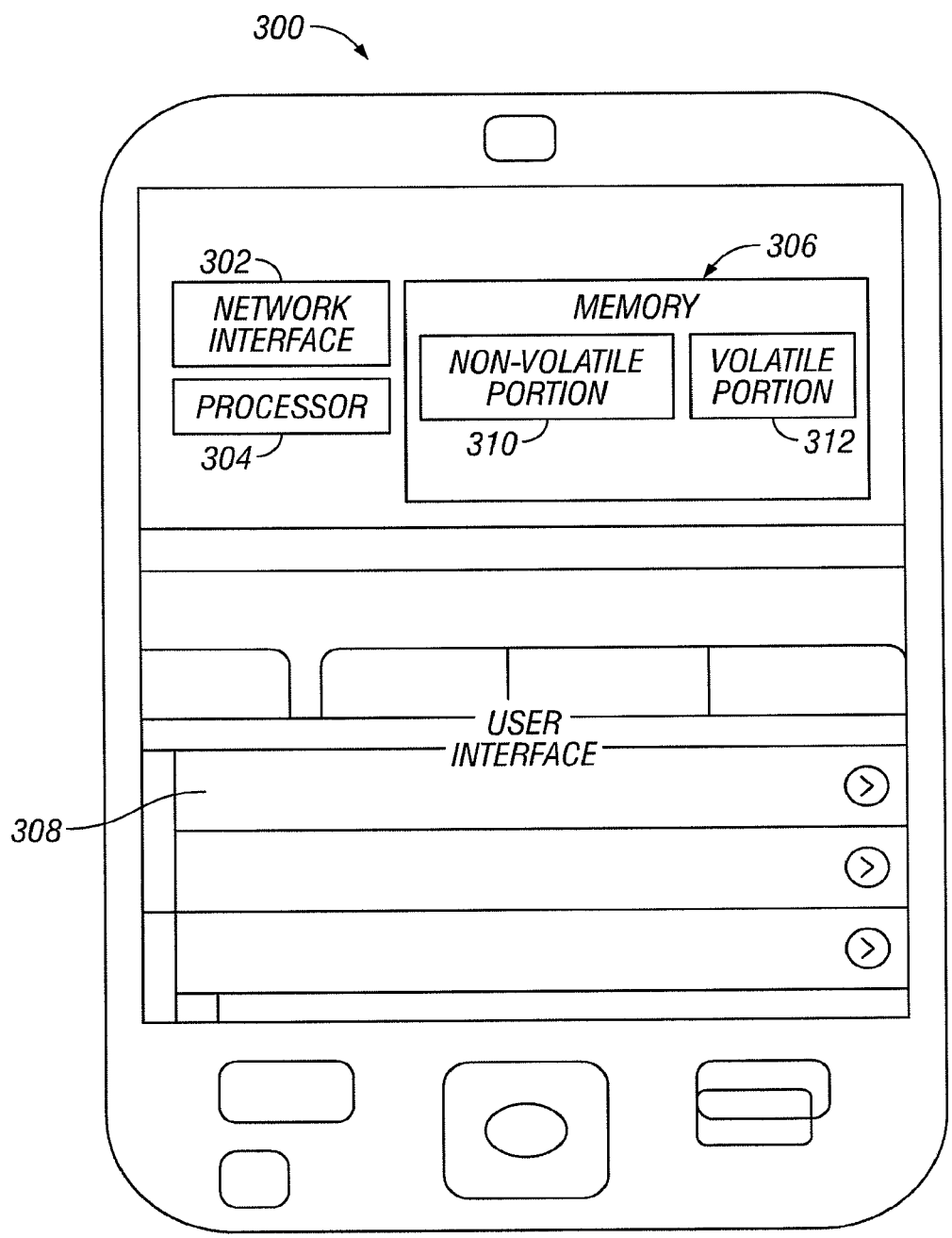
FIG. 3 is a block diagram illustrating an example embodiment of a handheld device for executing a medical information management application for displaying and tracking medical case information including medical chart information.

FIG. 3 is a block diagram illustrating a mobile device 300 representing an example embodiment of mobile device 118. As illustrated, mobile device 300 includes a number of components that operate together to facilitate the management of medical information. Mobile device 300 can support a number of different operations, including receiving practice location and user configuration information, case board information, medical chart information, patient treatment information, and case summary information for presentation and management on a graphical user interface. In addition, mobile device 300 may facilitate the transmission of alerts and tracking medical cases and medical charts. Mobile device 300 is further operable to facilitate the management of medical case assignments and roles through a graphical user interface. Additionally, mobile device 300 is capable of securely accessing medical case information from a remote medical information management system using appropriate authentication and secure access techniques.

As illustrated, mobile device 300 includes a number of components for maintaining and displaying medical information. Mobile device 300 may represent any suitable portable hardware, including appropriate controlling logic and data capable of communicating with remote devices and systems, receiving user input, and displaying medical information. As shown, mobile device 300 includes several components, which may include a network interface 302, a processor 304, a memory 306 and a user interface 308. The illustrated embodiment further discloses memory 306 as including a non-volatile portion of memory 310 and a volatile portion of memory 312.

Network interface 302 represents any appropriate combination of hardware and controlling logic for coupling to one or more networks. Network interface 302 may support any number of suitable protocols for communicating on a communication network. For example, network interface 302 may be a wireless local area network interface, cellular network interface, satellite interface, and/or any other appropriate interface for communicating on a communication network. Network interface 302 may have multiple interfaces for handling different communication protocols.

Processor 304 represents one or more processing elements, including hardware, logic, and data capable of controlling the operation of mobile device 300. For example, processor 304 may be a computer processor for executing a medical information management application stored in memory 306, or any other software or controlling logic associated with mobile device 300, such as a mobile operating system.

Memory 306 represents appropriate hardware and control logic for maintaining a medical information management application and case information including medical chart information corresponding to one or more medical practices. Memory 306 may also include storage for other data, such as a mobile operating system of mobile device 300. As illustrated, memory 306 includes a non-volatile portion 310 and a volatile portion 312. Non-volatile portion 310 of memory 306 represents memory for maintaining persistent applications and/or data. Volatile portion 312 of memory 306 represents storage for maintaining non-persistent applications and/or data. According to particular design considerations, the medical information management application and practice, location, and user configuration data may be stored in the non-volatile portion 310 of memory 306, while medical professional, location, practice activity, patient data, and case information including medical chart information retrieved from a medical information management system may be stored in the volatile portion 312 of memory 306. Such an implementation provides added security to critical data and helps to ensure that confidential user, patient, and/or case information is not readily accessible even if mobile device 300 is lost or otherwise compromised. In some implementations, some or all of the practice, location, and user credentials may be stored in non-volatile memory to facilitate seamless access and/or quick reentry into the system, while some other credential may be stored in volatile memory to ensure that a lost device cannot be improperly used.

Mobile device 300 also includes a user interface 308. User interface 308 represents any appropriate combination of hardware, control logic, and data for displaying information to a user and receiving inputs from a user. Thus, user interface 308 includes any input and/or output interface. For example, a user interface may be a touch screen interface that is capable of both displaying graphical information and receiving user inputs. User interface 308 of mobile device 300 may be used to display medical case information including medical chart information using a medical information management application, and receive real-time updates of such information for appropriate processing and forwarding by the medical information management application.

In particular embodiments, mobile device 300 is capable of transmitting, receiving, and modifying medical case information including medical chart information to track changes occurring in real-time at a medical facility and forward such information to a medical information management system. Mobile device 300 may be used by medical professionals to receive real-time information corresponding to one or more cases and enter real-time updates for transmission to a medical information management system. Such updates, in turn, can be delivered to other computing devices or systems. In particular embodiments, mobile device 300 must transmit updates to medical information management system 120, which controls whether data is actually updated. Thus, a handheld device, such as mobile device 300, enables medical case information to be managed and coordinated between medical professionals actively rendering care to one or more patients. For example, medical chart information may be periodically updated in real-time during a patient treatment episode.

In operation, elements of mobile device 300 perform various functions including facilitating maintenance and display of a graphical electronic medical chart, enabling entry and display of drugs, fluids, events, vital signs, physiological data, and laboratory information, facilitating recording of medical professional activity information and patient treatment records having case chronology information, permitting the transmission of alerts for tracked medical cases including notifications of incomplete data, providing an intuitive graphical user interface for interacting with the system, enabling tracking of medical case assignments and roles in addition to handing-off assignments and roles between medical professionals, and facilitating secure authentication and access techniques.

To provide a graphical case board including a medical chart, mobile device 300 retrieves and presents information maintained by medical information management system 120. For example, processor 304 may execute a medical information management application residing in a nonvolatile portion 310 of memory 306 to receive medical case board information. Once this information is received, mobile device 300 may display a graphical medical chart using user interface 308. In operation, user interface 308 may graphically present a medical chart having multiple predefined sections in predefined regions of the display. In particular embodiments, the medical chart is presented in a distinct tab which may be selected through the user interface 308. Other tabs may provide functionality such as case board, case summary, and checklist items as disclosed in U.S. patent application Ser. Nos. 12/789,783; 12/789,858; 12/789,900; 12/789,962; and Ser. No. 12/790,011.

In some embodiments, the predefined sections of the medical chart may correspond to drugs administered, fluids entering the patient and being expelled by the patient, events, vital signs such as blood pressure and heart beat, physiological patient information, and laboratory information. In certain embodiments, physiological patient information and laboratory information may be toggled on the display where one is shown at a given time depending on user selection. Each of the sections of the medical chart may be divided into time intervals and facilitate the recording of data values corresponding to the medical information being recorded. For example, in the drugs section, the values may correspond to a discrete dosage value or a dosage value over time, time of administration, or other appropriate values. On the other hand, the events section may facilitate the timestamp and type of event (e.g., tourniquet on). Thus, each section may permit the recording of values relevant for the section or particular sub-item of a section of the medical chart.

In operation, during each interval of time during a procedure, the medical care professional using the system may enter appropriate values in corresponding sections of the medical chart. For example, the user may enter an appropriate systolic and diastolic pressure for the current subinterval of time during a medical procedure. In certain embodiments, automated data seeding can be enabled, which may allow the user interface to automatically generate values for specific time intervals for later verification by the user. In such embodiments, the medical information management application may generate automatic values based on an algorithm or measured value for a current time interval if the user does not specify particular values. For example, the medical information management application may replicate the most recently recorded value for systolic and diastolic pressure and heart beat of the patient. In certain embodiments, according to particular policies of the medical care establishment, the medical information management application may indicate automatically generated information as incomplete, for example, by using a particular color scheme, a colored dot, shading the corresponding region, or other appropriate indicator. In some embodiments, users may select an incomplete data item to verify or adjust the data entry. In a similar fashion, data in various sections of the medical chart corresponding to drugs, fluids, events, vital signs, physiological data, or laboratory information may be entered by the user or automatically generated if automated data seeding is enabled.

In certain embodiments, the medical information management application may generate notifications based on the presence of incomplete data items. According to practice or procedure specific templates or policies, users of the system may be reminded of the presence of incomplete data. For example, after a predetermined period of time after completion of a patient treatment episode, the user responsible for data recording may be notified of the presence of incomplete data. In some embodiments, other medical care professionals (e.g., a supervisor) may also be notified as appropriate. Notifications may be in any appropriate form such as pop-up, text message, voice message, multimedia message or other suitable mechanism. Notifications may be layered such that various degrees of alerts are employed to encourage the user to complete the incomplete data. In particular embodiments, the notification layers are configurable according to practice or procedure specific templates or policies.

In certain embodiments, mobile device 300 may facilitate responding to alert messages, for example, to acknowledge the receipt of the alert or to otherwise engage other medical professionals to take appropriate action in response to the indicated case event. In those embodiments, the response may be received by user interface 308 and the medical information management application being executed by processor 304 may process the response for delivery to a remote medical information management system over a communication network using network interface 302. The medical information management system may then process the response and forward corresponding messages to one or more handheld devices and/or systems as appropriate.

This disclosure recognizes a particular method of presenting, on a display of limited size, complex medical data related to one or more patients. In some embodiments, this is performed by providing an interface capable of simultaneously displaying a subset of medical data related to a patient. The subset of data may be selected based on a template configured via web-based administrative capability and/or via mobile device interface. In some embodiments, such as the embodiment depicted in FIG. 4, the interface presents the subset of data according to a time-scale based chart. The subset of data can be presented graphically, numerically, and/or using alpha characters. By presenting the subset of data in such interface, an interpreter of such data (e.g., an anesthesiologist) is able to locate data of interest with less visual work and effort than would otherwise be required to locate data of interest in conventional interfaces configured to display medical data related to a patient.

While mobile device 300 is illustrated as including specific components, it should be understood that various embodiments may operate using any suitable arrangement and collection of components.

Figure 4:
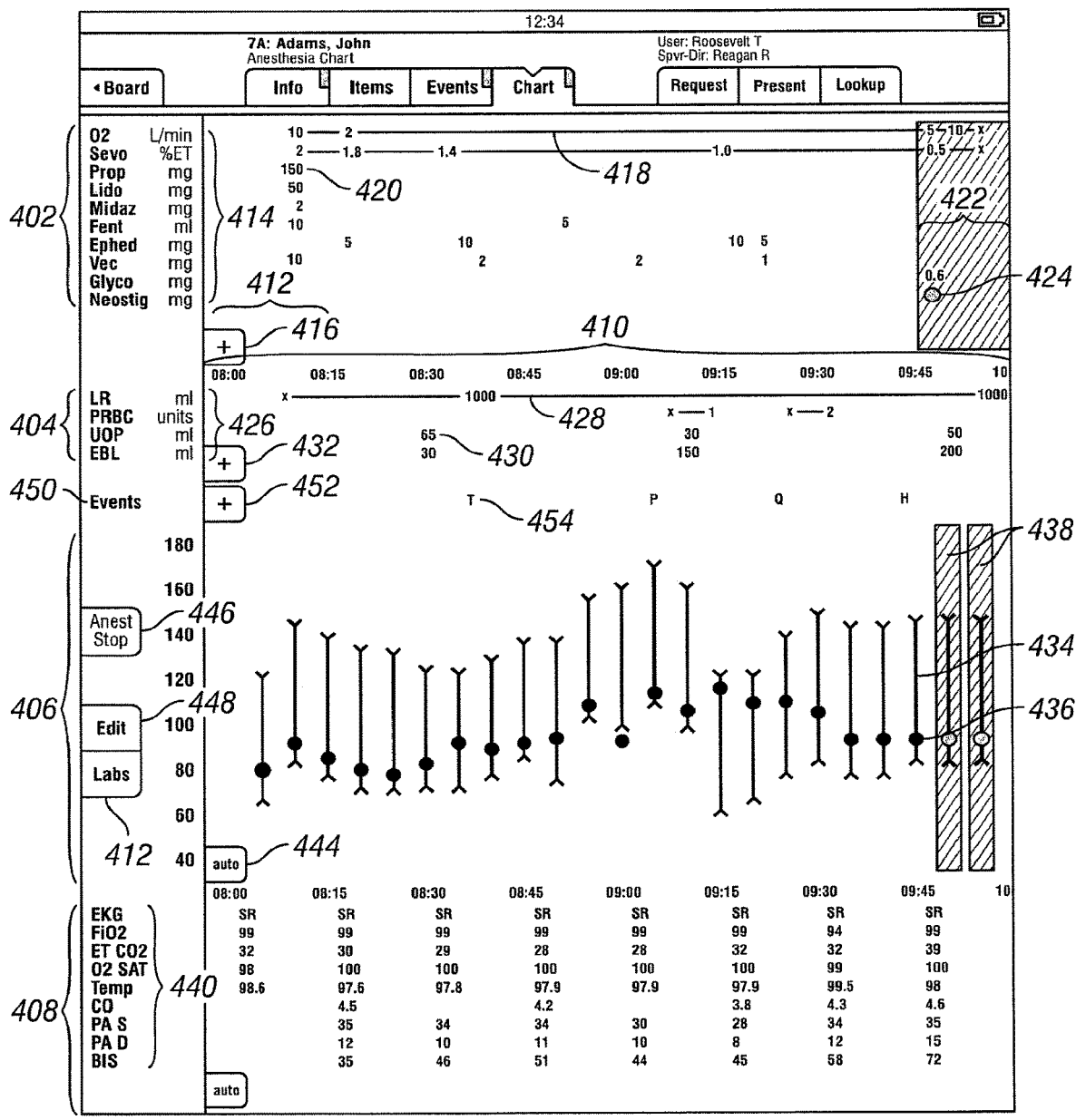
FIG. 4 is a system architecture diagram describing an example user interface for a medical chart facilitated by a medical information management application operating on a handheld device.

FIG. 4 is a diagram illustrating an electronic medical chart 400 representing an example medical chart interface for a hand held device interacting with a system according to the present disclosure. As shown, medical chart 400 includes various elements that together provide a user-friendly interface for interacting with the medical chart. In the illustrated embodiment, medical chart 400 is organized into multiple sections. For example, medical chart 400 includes a drugs display section 402, a fluids display section 404, a vital signs display section 406, and a physiological data display section 408. In system 400, each of these sections occupy a distinct area of the screen and are simultaneously viewable. Each of these sections span a maximum viewable time range 410. The maximum viewable time range 410 is further divided into equally distributed time intervals. In this embodiment, the maximum viewable time range is two hours spanning 8 a.m. to 10 a.m. The maximum viewable time range may correspond to the average length of a typical procedure at a particular medical care establishment. In other embodiments, the maximum viewable time range may vary between approximately thirty minutes and four hours. The maximum viewable time range 410 may be further divided into equally distributed time intervals. For example, maximum viewable time range 410 may be divided into fifteen minute time intervals. As shown, time interval 412 represents one of the equally distributed time intervals spanning 8 a.m. to 8:15 a.m. Each of the display sections display and facilitates recording of medical information about a particular patient undergoing a specific medical procedure. For example, in medical chart 400, the various sections displays and facilitates entry of information regarding the drugs, fluids, events, vital signs, monitored physiological information, and laboratory information related to a patient undergoing anesthesia.

In certain embodiments, although the information displayed may be limited to the maximum viewable time range 410, the user may horizontally scroll the display to show events occurring prior to the currently displayed time range. For example, if three hours has elapsed and the maximum viewable time range is two hours, the user may scroll back to view medical chart information for the first hour. In one embodiment, horizontal scrolling may be activated by swiping or providing suitable gestures on the screen in the intended direction (e.g., left or right) in appropriate areas of the screen. In some embodiments, a left or right gesture by the user in a non-shaded or non-colored region may activate horizontal scrolling. In those embodiments, shaded or colored regions may indicate regions that contain incomplete data and which can be activated to provide appropriate values to render the time interval or subinterval complete. Other embodiments may have distinct regions that facilitate horizontal scrolling and others that do not allow such scrolling.

Certain embodiments may facilitate identifying time intervals, subintervals or subsections of display section that contain incomplete data. An incomplete time interval, subinterval or subsection may be a current or past time interval, subinterval, or subsection of the display section that includes data that requires additional information or confirmation, such as partially completed entries, automatically populated entries, or data entered by rapid entry.

As illustrated, drugs display section 402 lists various drugs administrable to the current patient. The displayed list of drugs can be practice specific or procedure specific as appropriate. The displayed list of drugs may be defined by a template for the practice location or a particular user library selected by the user. In the illustrated embodiment, drugs display section 402 includes a drugs listing 414 specifying various drugs that may be administered during a medical procedure to the patient. Although drugs listing 414 shows ten drugs in this particular embodiment of medical chart 400, drugs listing 414 can include less or more than the drugs shown according to particular implementations. In certain embodiments, when drugs listing 414 is too long to be displayed simultaneously in the section allocated for drugs display section 402, the drugs listing 414 is vertically scrollable within the drugs display section 402. In those embodiments, vertical scrolling may cause the entire section may scroll accordingly to display the information corresponding to the drugs viewable on the screen. Drugs display section 402 also includes a add drugs button 416 which facilitates the addition or subtraction of drugs listed in drugs listing 414.

In the illustrated embodiment, two ways of entering drug related information into drugs display section 402 are shown. For example, drugs values may be entered as a dosage that spans time (i.e., a rate). For instance, drug rate entry 418 depicts the oxygen in liters per minute being administered to the patient over time. The solid lines indicate no change from the previous value and the in time that the value does change, a new value is shown. For example, as shown, O2 starts at ten liters per minute then changes to two liters per minute and then continues until it changes later to five liters per minute and then to ten. Drugs may also be entered as a fixed dosage value as shown by drugs amount entry 420. The illustrated drugs display section 402 also depicts an incomplete time interval 422 that spans the same duration as time interval 412 but represents the time interval starting at 9:45 a.m. to 10 a.m. As shown, incomplete time interval 422 is shaded to indicate that at least one value of data in time interval 422 is incomplete. In this particular example, time interval 422 is indicated as incomplete because of incomplete drug entry 424 shown as a colored dot in incomplete time interval 422. In this particular embodiment of medical chart 400, the fact that incomplete time interval 422 is shaded may indicate to the user that this time interval is editable such that the user may select this time interval and make an appropriate indication of the one or more appropriate values such that this time interval is rendered complete. In certain embodiments, only those time intervals indicating incomplete data can be selected by the user to enter or revise data values. In those embodiments, the remaining parts of medical chart 400 will not be immediately editable to the user.

Medical chart 400 also illustrates a fluids display section 404. Fluids display section 404 represents the section on medical chart 400 for displaying and recording all fluids that either enter or are expelled by the patient. In this example, fluids display section 404 displays four fluids in fluids listing 426. Fluids display section 404 facilitates entry either by values over time or as discrete values at a particular time. For example, fluids entry 428 indicates a value for a particular fluid being administered over a span of time whereas fluids entry 430 shows a discrete amount of fluid at a particular time. Fluids display section 404 also includes an add fluids button 432 that facilitates the addition or removal of fluids listed in fluids listing 426. As with drugs listing 414, fluids listing 426 can be vertically scrollable if the number of fluids listed in fluids listing 426 exceeds the area allocated for fluids section 404. In those embodiments where fluids listing 426 is scrollable the entire section responds to such scrolling such that the values corresponding to the displayed drugs are shown in this section.

Vital signs display section 406 represents the section of medical chart 400 that displays vitals signs corresponding to the patient. In this particular example, the vital signs that are recorded are the blood pressure and heart rate of this particular patient. In certain embodiments, vital signs of the patient may be recorded at a higher frequency than the data recorded in other sections of medical chart 400. For example, in vital signs display section 406, the vital signs of the patient are recorded at five minute intervals such that there are at least three recordings within each fifteen minute time interval. In this embodiment, blood pressure is recorded as a line segment as depicted by blood pressure line segment 434. As illustrated, blood pressure line segment 434 spans a systolic pressure of approximately one hundred fifty and a diastolic pressure of approximately eighty. Vital signs display section 406 also displays the heartbeat of the patient in intervals of five minutes. In this example, heartbeat indicator 436 shows a heartbeat of approximately ninety. In this embodiment of vital signs display section 406, two incomplete vital signs sections 438 are shown. Both of these subsections are shaded to indicate that data in those subsections are incomplete.

In particular embodiments where automated data seeding is enabled, vital signs are automatically generated according predetermined algorithm as the current time progresses. For example, in certain embodiments, the automatically generated vital signs values may relate to the last recorded vital signs values. For example, incomplete vital signs subsections 438 both replicate the same value indicated by blood pressure line segment 434 and heartbeat indicator 436. In this embodiment, incomplete vital signs subsections 438 are user selectable for editing purposes to either verify the data or to change the value to the appropriate value for this patient for the corresponding time.

As illustrated, medical chart 400 also includes a physiological data display section 408. Physiological data display section 408 facilitates display and recording of physiological data related to the patient. As shown, physiological data display section 408 includes a monitored values list 440 which represents various physiological information related to the patient. As with the other display sections, physiological data corresponding to the patient can be entered for each of a plurality of time intervals, such as time interval 412. Medical chart 400 also includes a labs button which facilitates toggling between the physiological data display section 440 and another display related to laboratory information corresponding to the patient. By selecting the labs button 442, the user can quickly view lab values corresponding to the patient that might be relevant for the patient's care. By selecting the labs button 442 for a second time the user may be returned to the physiological data display section 408. In other embodiments, both the physiological data display section and the laboratory information may be simultaneously viewable on the display.

Medical chart 400 in the illustrated embodiment, includes an auto-population indicator 444. The auto-population indicator 444 indicates whether medical data that is recorded on a periodic time interval will be auto-populated based on one or more algorithms. As discussed above, vital signs information may be auto-populated on a periodic basis such as five minutes in certain embodiments. For example, when auto-population takes place, the vital signs of a patient may replicate the previously recorded value or be some measured value obtained from the patient. For instance, the vital signs information displayed in incomplete vital signs subsections 438 indicate values that replicate the values represented by blood pressure line segment 434 and heartbeat indicator 436. In some embodiments, auto-population of data values may render those data values incomplete, which may be indicated by a suitable indicator, such as a color scheme, shading, or specific shapes (e.g., dots). In such instances of incomplete data, verification or adjustment may be required by the user to finalize those values. In particular embodiments, medical chart 400 also includes a next event indicator 446. As depicted, the next approaching event is anesthesia stop. In particular embodiments, selecting the next event indicator causes the user interface to transition to the next event. For example, selecting anesthesia stop may end the current patient treatment episode.

Medical chart 400 may also include an event section 450. In the illustrated embodiment, events may represent actions that take place during the treatment of a patient. Events may include actions that may be needed as particular circumstances arise and may not be necessary for every patient or medical procedure. For example, as depicted, the first event is a tourniquet event 454 that took place at approximately 8:40 a.m. Thus, the event section 450 enables the user to enter events that may or may not occur in the ordinary course but may be necessary during the treatment of a particular patient. In this embodiment, add events button 452 allows the user to enter specific events during the course of a medical procedure. By selecting add events button 452, the user is presented with a predefined list of common events to select from or the user may alternatively select from a library of all events that might be practice or procedure specific as configured by particular templates.

Embodiments of the present disclosure provide charted data regions or sections having modular vertical sections for distinct presentation of data items for drugs, fluids, events, vital signs and monitored physiologic data. In certain implementations, data items for each section may contain multiple data elements such as time of administration, type of administration, and dose of administration. According to particular embodiments, data item elements may be optional or required by the medical care establishment and may be configurable via a web-based administrative capability.

Data entry on a handheld apparatus according the present disclosure may be by finger touch or by any other appropriate input means such as a pen, stylus, keyboard, mouse, or other suitable touch screen gesture control or user input mechanism. In certain embodiments, the dimensions of the various sections of the medical chart may be determined based on the input method. For example, if finger touch is the preferred input method, the dimensions may be larger than if a stylus or mouse were being used. In addition, the dimensions of the sections of the medical chart may be adjusted in real-time to account for overages in data recording. For example, if the number of drugs being recorded exceeds the number of drugs that can be shown on the display at one time and other sections such as the monitored physiological data section has only a few data items, the system may dynamically adjust the dimensions of the two sections such that most of the recorded information can be visually displayed simultaneously on the screen. Thus, sections of the medical chart may be dynamically scaled up or down to accommodate data overages or reductions in one or more sections or based on the input mechanism.

While medical chart 400 is illustrated as including specific elements, it should be understood that various embodiments may implement an electronic medical chart interface using any appropriate combination of elements for providing for facilitating the display and recording of medical information related to a patient.

Figure 5:
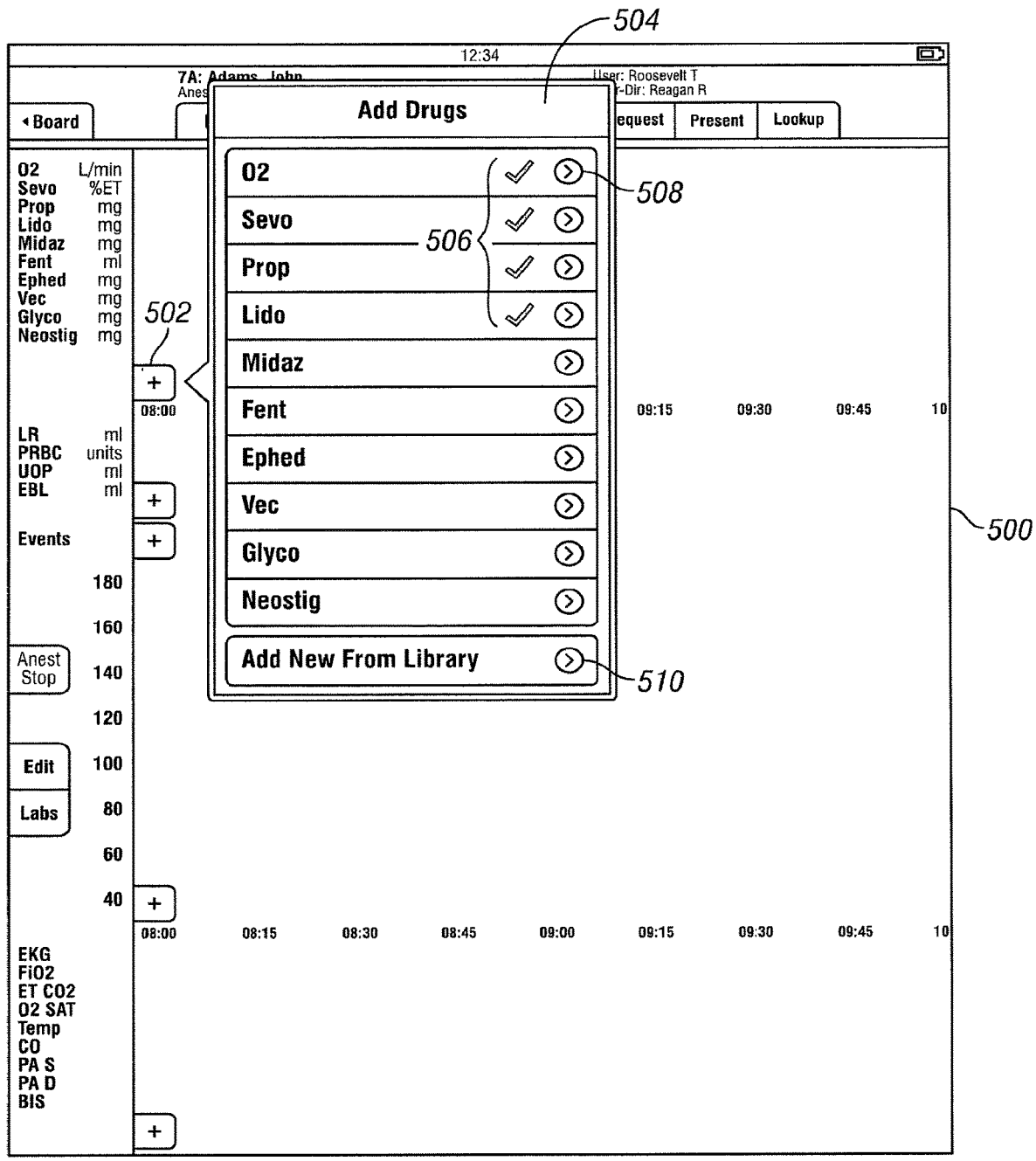
FIG. 5 illustrates an example view for adding drug tracking information to an electronic medical chart through a graphical user interface of a handheld device.

FIG. 5 is an add drugs view illustrating a particular embodiment of the electronic medical chart according to the present disclosure. In the illustrated embodiment, various features of system 500 are shown. For example, system 500 depicts an add drugs button 502, add drugs display 504, rapid entry indicators 506, edit drugs value selector 508, and add new drugs from library selector 510. System 500 facilitates the entry of drugs onto the electronic medical chart such that drugs being administered to a patient can be recorded and displayed.

In operation, selecting the add drugs button causes the add drugs display 502 to appear as shown. A user of the medical chart may select one or more drugs as appropriate for through the interface. In a particular embodiment, the user may opt for rapid entry of the displayed drugs by selecting the drugs but without specifying the particular values corresponding to the drug being administered. This may allow the user to quickly track the drugs being administered and permit the user to complete the actual values for those drugs at a later time at the user's convenience. In this manner, acute patient care may be prioritized over documentation. In certain embodiments, the rapid entry indicators 506 provide a visual indication to the user regarding the drugs selected. In the illustrated embodiment, selecting the first four drugs causes a check mark to be displayed next to each of those drugs. According to particular embodiments, the user may return to the medical chart to view or record other medical information without entering a specific value for the drugs. The medical chart may provide an appropriate indication of incomplete data in the time interval associated with a rapid entry of drugs, such as a colored dot for each drug or other appropriate indicator. Alternatively, the user may enter specific values for the drugs being administered to the patient by selecting edit drugs value selector 508. Selecting the edit drugs value selector 508 may cause system 500 to present a separate screen to allow the user to select from common values of the drug or to enter a specific value for the drug. In some embodiments, system 500 may include an add new drugs from library selector 510 which allows the user to add drugs to add drugs display 504. The library displayed may be configurable according to the practice or the current medical procedure being performed.

While system 500 is illustrated as including specific elements, it should be understood that various embodiments may implement an electronic medical chart interface using any appropriate combination of elements for providing for facilitating the display and recording of medical information related to a patient.

Figure 6:
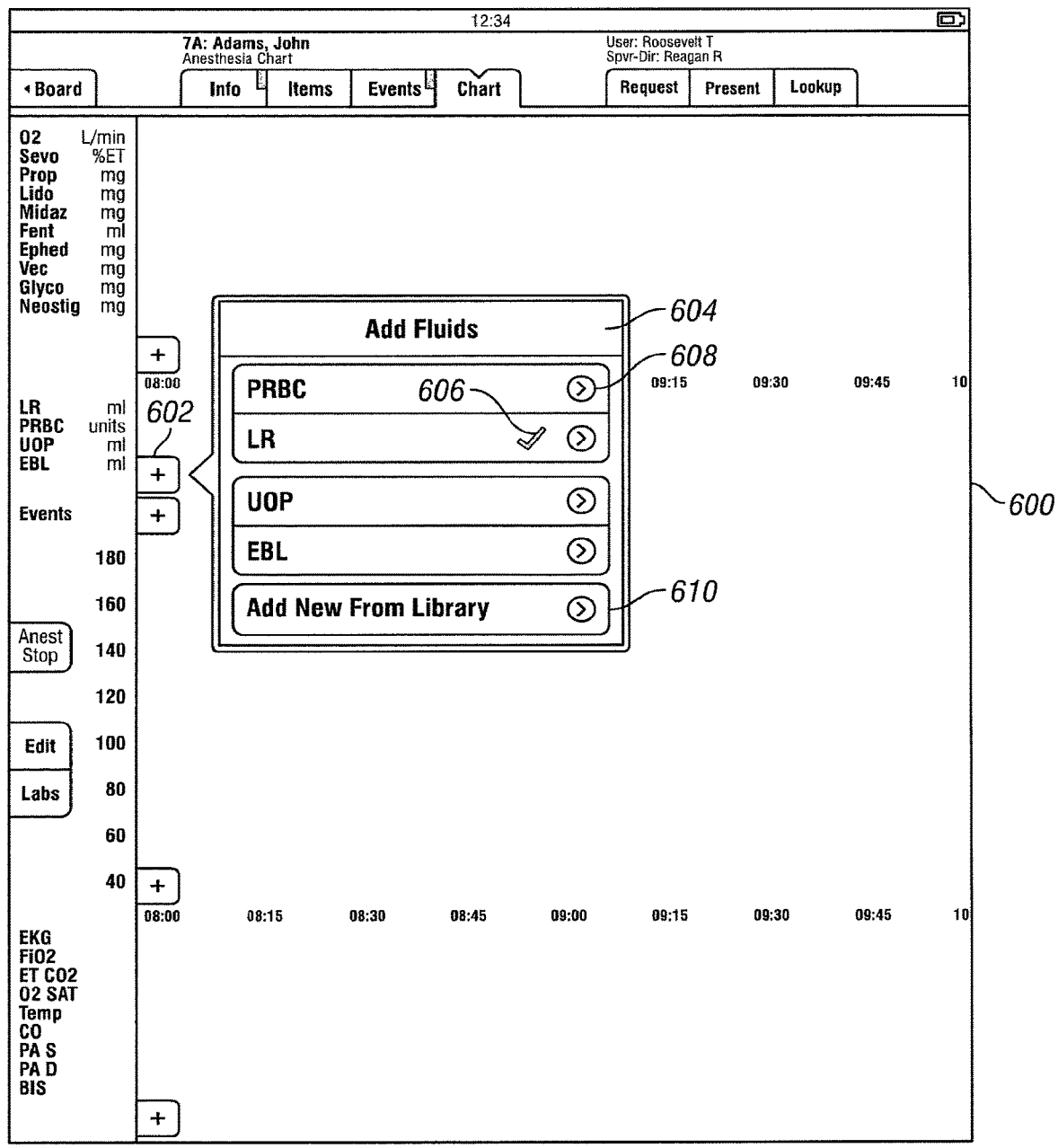
FIG. 6 illustrates an example view for adding fluid tracking information to an electronic medical chart through a graphical user interface of a handheld device.

FIG. 6 is an add fluids view illustrating a particular embodiment of the electronic medical chart according to the present disclosure. In the illustrated embodiment, various features of system 600 are shown. For example, system 600 depicts an add fluids button 602, add fluids display 604, rapid entry indicator 606, edit fluids value selector 608, and an add new events from library selector 610. System 600 facilitates the entry of fluids onto the electronic medical chart such that fluids entering or being expelled by the patient can be recorded and displayed.

In operation, selecting the add fluids button causes the add fluids display 602 to appear as shown. A user of the medical chart may select one or more fluids as appropriate for through the interface. In a particular embodiment, the user may opt for rapid entry of the displayed by selecting the fluids but without specifying the particular values corresponding to the fluids entering or leaving the patient. This may allow the user to quickly track fluids and permit the user to complete the actual values for those fluids at a later time at the user's convenience. In certain embodiments, the rapid entry indicators 606 provide a visual indication to the user regarding the fluids selected. In the illustrated embodiment, selecting the second fluid causes a check mark to be displayed next to the fluid. According to particular embodiments, the user may return to the medical chart to view or record other medical information without entering a specific value for the fluids selected. The medical chart may provide an appropriate indication of incomplete data in the time interval associated with a rapid entry of fluids. Alternatively, the user may enter specific values for the fluids being administered to the patient by selecting edit fluids value selector 608. Selecting the edit fluids value selector 608 may cause system 600 to present a separate screen to allow the user to select from common values of the fluid or to enter a specific value for the fluid. In some embodiments, system 600 may include an add new fluids from library selector 610 which allows the user to add fluids to add fluids display 604. The library displayed may be configurable according to the practice or the current medical procedure being performed.

While system 600 is illustrated as including specific elements, it should be understood that various embodiments may implement an electronic medical chart interface using any appropriate combination of elements for providing for facilitating the display and recording of medical information related to a patient.

Figure 7:
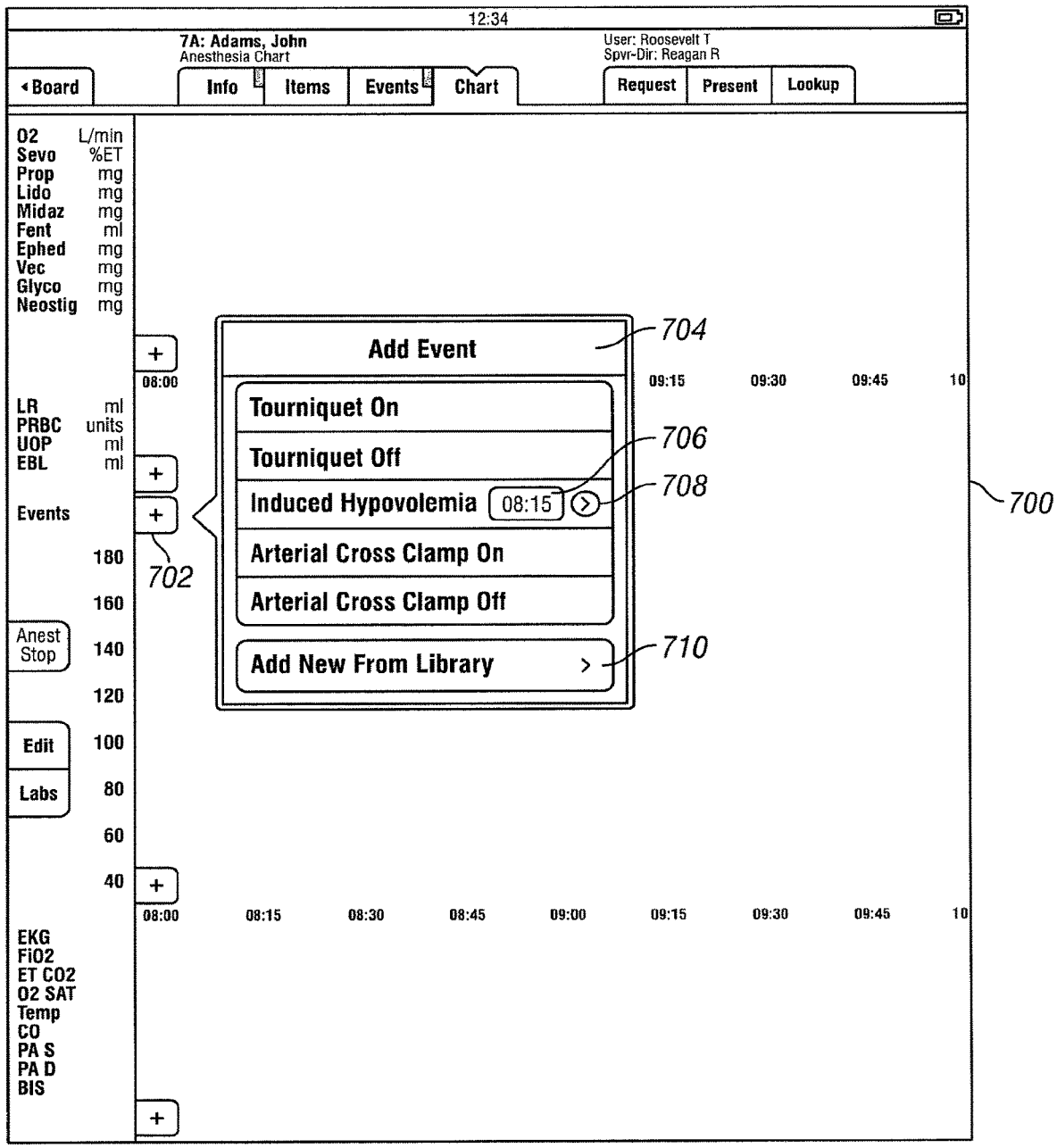
FIG. 7 illustrates an example view for adding events to an electronic medical chart through a graphical user interface of a handheld device.

FIG. 7 is an add events view illustrating a particular embodiment of the electronic medical chart according to the present disclosure. In the illustrated embodiment, various features of system 700 are shown. For example, system 700 depicts an add events button 702, add events display 704, current time indicator 706, edit events value selector 708, and an add new events from library selector 710. System 700 facilitates the entry of events onto the electronic medical chart such that events related to the patient's care can be recorded and displayed.

In operation, selecting the add events button causes the add events display 702 to appear as shown. A user of the medical chart may select one or more events as appropriate for the medical procedure through the interface. In a particular embodiment, selecting a particular event may cause the current time to be displayed next to the event. For example, the current time indicator 706 next to "Induced Hypovelemia" in add events display 704 shows a current time of 8:15. The user may opt to accept this time value and return to the medical chart to view or record other related medical information. Alternatively, the user may change the specific time value for the selected event by selecting edit events value selector 708. Selecting the edit events value selector 708 causes system 700 to present a separate screen to allow the user to select an appropriate time value for the event. In some embodiments, system 700 may include an add new events from library selector 710 which allows the user to add events to add events display 704. The library displayed may be configurable according to the practice or the current medical procedure being performed.

While system 700 is illustrated as including specific elements, it should be understood that various embodiments may implement an electronic medical chart interface using any appropriate combination of elements for providing for facilitating the display and recording of medical information related to a patient.

Figure 8:
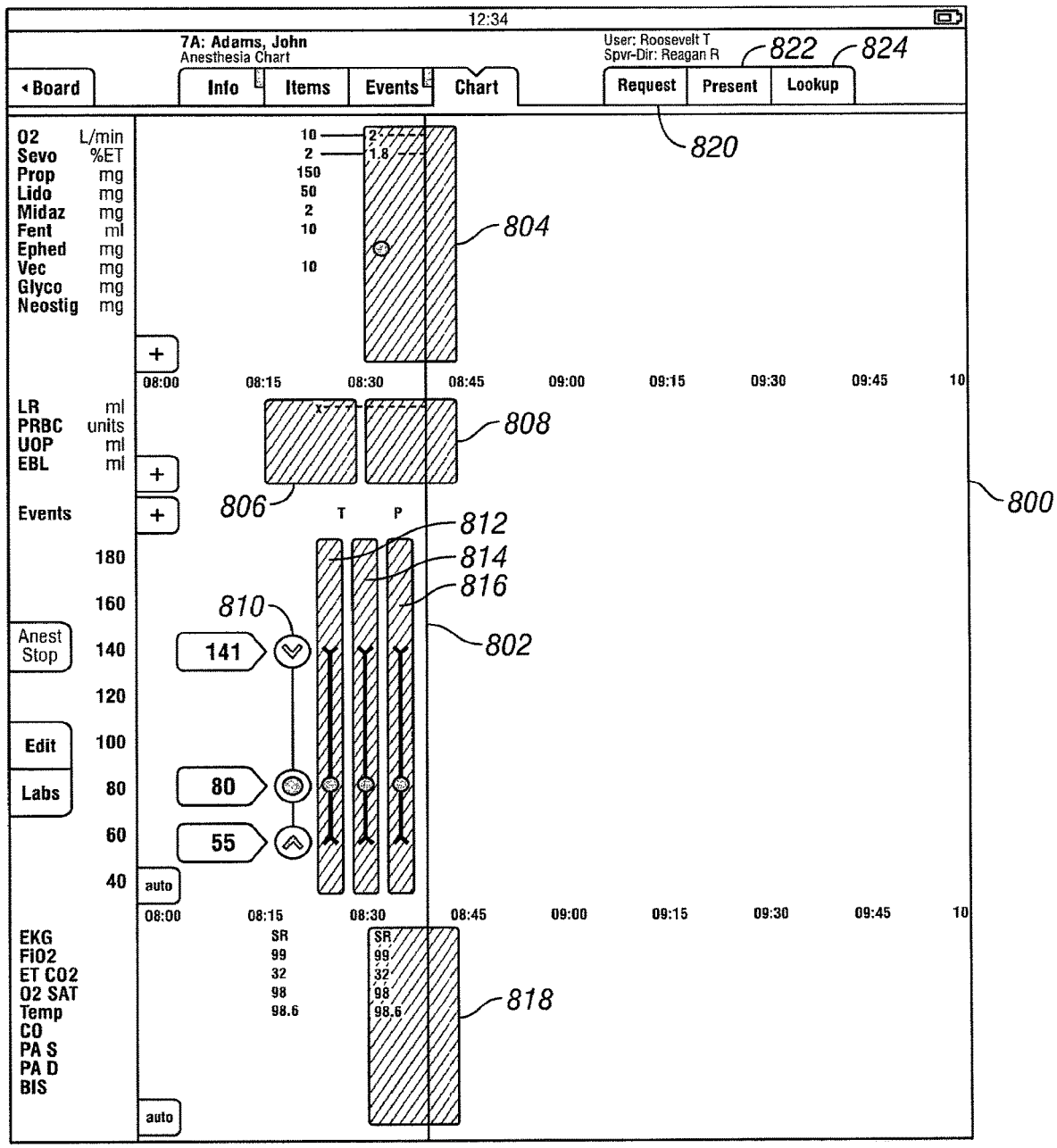
FIG. 8 illustrates an example view displaying incomplete data on an electronic medical chart presented through a graphical user interface of a handheld device.

FIG. 8 is an automated data seeding view of a particular embodiment of the electronic medical chart according to the present disclosure. In the illustrated embodiment, various aspects of system 800 are shown. For example, system 800 depicts a current time tracker 802, an incomplete drugs time interval 804, a first incomplete fluids time interval 806, a second incomplete fluids time interval 808, vital signs editor 810, a first incomplete vital signs time interval 812, a second incomplete vital signs time interval 814, a third incomplete vital signs time interval 816, an incomplete monitored values time interval 818, a request button 820, a present button 822, and a lookup button 824. System 800 illustrates various examples of automated data seeding in different sections of the electronic medical chart. Particular values used in automated data seeding can be determined according to a suitable algorithm. For example, a particular implementation of automated seeding may replicate the last previously recorded value. In another example, the value may be ascertained through measurement using appropriate instruments or by assessing the patient. In particular embodiments, the use of automated data seeding may cause the data item to be indicated as incomplete and require the user to verify or adjust the automatically generated data value at an appropriate time.

In certain embodiments, the activation of automated data seeded may be conditioned on a medical milestone being entered (e.g., anesthesia start or enter operating room). In certain embodiments, once automated data seeding is activated, it may proceed until a later medical milestone is reached (e.g., anesthesia stop or exit operating room). Such conditions for automated data seeding activation and deactivation may be configured by an administrator using the web-based administrative capability. Moreover, the data elements that may be automatically seeded and frequency of automated data seeding (e.g., every five minutes or every fifteen minutes) may also be configurable.

As shown, current time tracker 802 indicates the current time according to the medical chart. In certain embodiments, current time tracker 802 may slide horizontally across the page to keep track of the current time. Current time tracker 802 may act as a boundary for automated seeding of data by not allowing any automated seeding for times in the future. For example, in the depicted embodiment, no automated seeding takes place to the right of current time tracker 802. As illustrated, system 800 also includes an incomplete drugs time interval 804 which is shaded to indicate that it contains incomplete data. Incomplete drugs time interval 804 demonstrates how automated data seeding for drugs may take place in a particular embodiment. For example for the first two drugs, the medical chart automatically selects values of two and 1.8, respectively. These values may be verified by the user at an appropriate time. In this example, the values that were automatically generated for incomplete drugs time interval 804 differ from the previously recorded values. As discussed above, the data values automatically generated may be defined by a suitable algorithm or measured using appropriate medical instruments or equipment. System 800 also includes a first incomplete fluids time interval 806 and a second incomplete fluids time interval 808. As depicted, both time intervals are shaded in this particular embodiment to indicate that they contain incomplete data. Time intervals 806 and 808 demonstrate the automated seeding of fluids in a particular embodiment. For example, for the first fluid, the medical chart automatically holds a value of 1000 ml across time intervals 806 and 808. This value may be verified by the user at an appropriate time.

In the vital signs display section, system 800 illustrates a particular embodiment of vital signs editor 810. In operation, a user can employ vital signs editor 810 to adjust the endpoints corresponding to the systolic and diastolic blood pressure of the patient. In this fashion, the user can specify the correct values for the blood pressure of the patient at a particular subinterval of time within a time interval. Similarly, the user can employ vital signs editor 810 to adjust the heat beat by sliding the dot associated with the heart beat in the appropriate direction to increase or decrease the value. As shown, system 800 also illustrates a first incomplete vital signs time interval 812, a second incomplete vital signs time interval 814, and a third incomplete vital signs time interval 816. In particular embodiments, these time intervals are shaded to indicate that they contain incomplete data to be verified by the user. In certain embodiments, the blood pressure and heart beat values depicted in time intervals 812, 814, and 816 have automatically seeded values. As discussed above, these values may reflect the most recently recorded value, measured values, or the results of any suitable algorithm. For example, in the depicted embodiment, time intervals 812, 814, and 816 each have values that correspond to the previously recorded values of blood pressure and heart beat of the patient.

In the monitored values section, system 800 shows an incomplete monitored values time interval 818. In particular embodiments, time interval 818 is shaded to indicate that it contains incomplete data that must be verified or adjusted by the user. As illustrated, time interval 818 may contain automatically seeded values for physiological data associated with the patient. For example, in the depicted embodiment, time interval 818 contains automatically seeded values that reflect the most recently recorded values for each line of physiological data.

While system 800 is illustrated as including specific elements, it should be understood that various embodiments may implement an electronic medical chart interface using any appropriate combination of elements for providing for facilitating the display and recording of medical information related to a patient.

Figure 9:
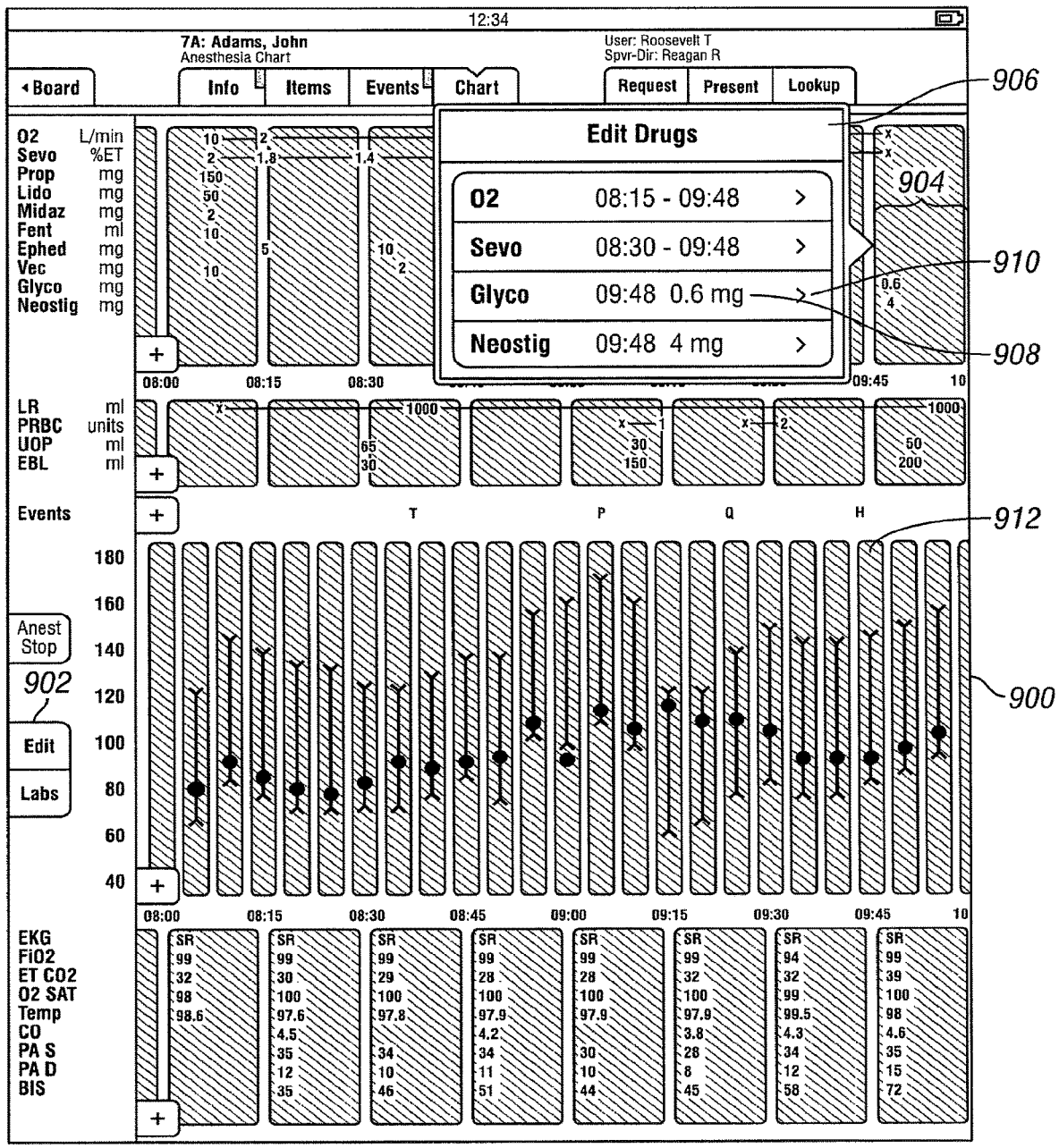
FIG. 9 illustrates an example edit view of an electronic medical chart presented through a graphical user interface of a handheld device.

FIG. 9 is an edit mode of a particular embodiment of the electronic medical chart according to the present disclosure. In the illustrated embodiment, various aspects of system 900 are shown. For example, system 900 depicts an edit button 902, an editable time interval 904, an edit drugs display 906, a current drugs value 908, a drugs value selector 910, and a vital signs subinterval 912. System 900 illustrates an edit mode of the medical chart where all time intervals and subintervals are accessible for editing by the user. The user may select any time interval, such as editable time interval 904, to edit values in a particular section of the medical chart.

In operation, a user may enter an edit mode of the medical chart by selecting the edit button 902. In particular embodiments, edit button 902 may be toggled between regular and edit modes. In certain embodiments, when in regular mode, time intervals and subintervals having incomplete data may be selected for editing by the user. In edit mode, any time interval or subinterval of time may be selected for editing by the user. As illustrated, selecting edit button 902 causes all time intervals and subintervals of time to be shaded, indicating that they are available for editing. For example, time interval 904 may be activated by the user causing edit drugs display 906 to be presented. As shown, edit drugs display section includes a time range and a current drug value corresponding to the time range for each drug. For example, current drug value 908 indicates a drug value of 0.6 mg which can be edited by the user. For example, a drugs value selector 910 may be activated by the user to change the current drug value 908. The user may then be presented with an interface for selecting among common values or specify a particular value. System 900 also illustrates a vital signs subinterval 912 which can be activated by the user to edit the blood pressure and heart beat values for the patient corresponding to that time subinterval. As illustrated, the vital signs may be recorded on a more frequent schedule (e.g., every five minutes) compared to time intervals (e.g., every fifteen minutes) in other sections of the medical chart.

As illustrated, system 800 also includes a request button 820, a present button 822, and a lookup button 824. These interfaces may provide auxiliary functions for the medical chart interface of system 800. In particular implementations, request button 820 may provide the user with a list of canned texts messages, such as simple message service (SMS) messages, for communicating with other individuals. In other implementations, the request button 820 may provide the user with the ability to send a user specified text message to a user. Some implementations may facilitate other forms of messaging including voice, instant message, page, multimedia message, or other appropriate messaging means. The present button 822, in particular embodiments, may provide a user-friendly mechanism to notify others that the user is presently attending to the patient and actively monitoring the patient's condition. The presence of a user may be delivered by voice, text, instant message, multimedia message, or other appropriate delivery mechanism. In particular embodiments of system 800, the lookup button 824 may provide users with a list of commonly used documents such as protocol documents, procedure documents, medical cross-reference charts, or directories (e.g., phone numbers and/or extensions). Thus, the lookup button may provide a convenient location for auxiliary information that may become helpful during active patient care. The specific documents that are presented when the lookup button 824 is activated may be template or protocol driven. Thus, a the documents listed may be specific to a medical care establishment, organization, or the medical procedure being performed.

While system 800 is illustrated as including specific elements, it should be understood that various embodiments may implement an electronic medical chart interface using any appropriate combination of elements for providing for facilitating the display and recording of medical information related to a patient.

Particular embodiments may facilitate the management and notification of incomplete data. As discussed, incomplete data may be present on the medical chart due to prioritization of acute patient care over documentation. In some embodiments, users may continue work on other cases even when incomplete data exists. In those cases, the users and others may be reminded of the presence of incomplete data. Incomplete data may exist as a result of rapid data entry, automated data seeding, or a user decision not to complete a required data item to prioritize patient care or for other reasons. Incomplete data that requires user attention may be configured by the medical establishment, medical organization, or administrator. In some cases, the designation of incomplete data may be driven by the circumstance, medical procedure, or nature of the data element. For example, some incomplete data, such as the patient's date of birth, may be derived from other medical systems while other information, such as vital signs for a specific time interval, may require immediate attention by the user to ensure accuracy and completeness. A medical care establishment or medical organization may require that certain data is entered by the user. For example, an organization may stipulate that all cases require a post-operation note or time to be recorded. In those cases, the user will be presented with notifications on every case where this information is incomplete. In other instances, case circumstances may determine whether a particular data element must be completed. For example, case circumstances may dictate that the drug lidocaine be administered. In this situation, once the administration of lidocaine is noted by the user, the user may be prompted later for completion of all required aspects for that lidocaine administration such as dose, method of administration, and time of administration.

Certain embodiments may allow multiple layers of notification to encourage users to appropriately address incomplete data values. The layers of notification may be user configurable and may enable notifications to be generated to other medical personnel such as nurses, supervisors, or hospital administrators. For example, in a first layer of notification, subtle visual reminders during data entry and review may be employed to identify incomplete data regions that may be edited by the user. In certain embodiments, such visual reminders may include colored text, shaded regions, flags, and/or specific color schemes. For instance, the use of red text, red shaded regions, or red flags may indicate that the corresponding data item is incomplete. In some embodiments, a colored flag (e.g., red flag) may appear on the tab corresponding to a category of medical information (e.g., chart) to indicate that a data item corresponding to the tab contains incomplete data. In this manner, a user may visually recognize that incomplete data exists in particular tabs even if the user is not currently viewing one of those tabs. This facilitates a high level view of categories of medical information that contain incomplete data that the user may need to address. In a similar fashion, colored flags may be used in the margins of particular sections of category of medical information to indicate regions in which incomplete data exists.

Other embodiments may include a second layer of notification where a more prominent notification is generated. For example, the user may be notified at the end of a patient care episode or when the user attempts to logout if incomplete data still remains. In those instances, the user may receive an alert that is accompanied by a sound or vibration which can be configured by the medical care establishment or by an administrator. In some embodiments, the user alert may involve a pop-up window indicating the specific elements of incomplete data and present navigation options for completing the incomplete data.

Particular embodiments may include a third layer of notification where an alternate notification pathway is used to notify the user and others of the presence of incomplete data. For example, the user may be notified by text message, email, instant message, page, pop-up, multimedia message, large screen display highlight, printed output box listing, automated phone call, or other appropriate notification mechanisms. Such notifications may be user configurable. For example, a medical care establishment may require such notifications to occur at periodic time intervals after completion of a patient care episode if certain data still remains incomplete. In those instances, the user may receive an alert that is accompanied by a sound or vibration which can be configured by the medical care establishment or by an administrator. In some embodiments, the user alert may involve a pop-up window indicating the specific elements of incomplete data and present navigation options for completing the incomplete data.

Although the present disclosure describes several embodiments, it should be understood that a myriad of changes, substitutions, and alterations can be made without departing from the spirit and scope of the invention as defined by the appended claims.

What is claimed is:

1. A handheld apparatus for updating an electronic medical record for a patient, the apparatus comprising:
　a display capable of receiving touch-responsive user input;
　a memory maintaining a medical information management application;
　a wireless network interface capable of coupling to a medical information management system operable to maintain a plurality of patient monitoring worksheets;
　a processor operable, when executing the medical information management application, to:
　　retrieve, from the medical information management system, a patient monitoring worksheet displaying a subset of medical information relating to the delivery of medical care to a first patient;
　　present, on the display, the retrieved patient monitoring worksheet, the patient monitoring worksheet having a maximum viewable time range selected from the range of thirty minutes to four hours and equally divided into a plurality of time intervals, and wherein the patient monitoring worksheet comprises a plurality of simultaneously viewable display sections comprising a drugs display section, a fluids display section, a vital signs display section, and a physiological data display section;
　　the drugs display section having a column listing a plurality of drugs and, for each of the drugs, a row capable of tracking of an amount of the drug administered for each of the time intervals, and wherein if a number of the drugs exceeds a drug list threshold, the drugs display section is vertically scrollable in response to touch-screen gesture control;
　　the fluids display section having a column listing of a plurality of fluids and, for each of the fluids, a row capable of tracking of an amount of the fluid administered or expelled for each of the time intervals, and wherein if a number of the fluids exceeds a fluid list threshold, the fluids display section is vertically scrollable in response to touch-screen gesture control;
　　the vital signs display section having a column indicating a scale and capable of tracking, for each of the equally distributed subintervals of time, a heart rate and a blood pressure of the patient charted on the scale; and
　　the physiological data display section having a column listing a plurality of physiological data items and, for each of the physiological data items, a row capable of tracking a value for the physiological data item for each of the time intervals, and wherein if a number of the physiological data items exceeds a physiological data item list limit, the physiological data display section is vertically scrollable in response to touch-screen gesture control;
　　wherein each of the time intervals of each of the display sections is a subsection;
　　detect a beginning of a new time interval;
　　identify a first subsection configured to auto-populate a value;
　　upon determining a first value for the first subsection, auto-populate the first subsection with the first value;
　　determine, for each subsection, whether information tracked during that subsection is incomplete and whether information corresponding to that subsection includes an auto-populated value;
　　detect touch-screen input selecting a subsection with one or more of incomplete information or auto-populated values; and present, in a portion of the display, an edit popup for the selected subsection, an edit popup permitting one or more of editing or verification of values for information tracked in the subsection;
determine, based on user input, an edited or verified value for the selected subsection; and
update the patient monitoring worksheet for the first patient by causing the edited or verified value to be stored by the medical information management system.

2. The apparatus of claim 1, wherein the processor is further operable, when executing the medical information management application to:
determine that a predefined time has passed after completion of a patient care associated with the patient monitoring worksheet;
determine one or more of the subsections having one or more of incomplete tracked information or an auto-populated value; and
communicate a notification indicating one or more of incomplete tracked information or an occurrence of an auto-populated value.

3. The apparatus of claim 1, wherein the first value is determined based on one or more of an algorithm or a measure.

4. The apparatus of claim 1, wherein the plurality of display sections further comprises an events display section and wherein the processor is further operable, when executing the medical information management application:
to detect a touch-screen input selection of a subsection of the events display section;
to present in a portion of the display an events edit popup for the selected subsection of the events display section, the events edit popup permitting selection of an event to be tracked in the subsection;
to transmit the selected event and a corresponding timestamp to the central medical information management system; and
to update the subsection of the events display section with a visual indication of the entered event.

5. The apparatus of claim 1, wherein the edit popup presents items trackable in the selected subsection, and wherein the processor is further operable, when executing the medical information management application, to:
receive a selection of a rapid entry indicator of one or more of the items trackable in the selected subsection;
determine that numeric values accompanying those items are required;
receive a confirmation of the selected items without receiving numeric values for one or more of the selected items;
visually indicate each of the selected items in the corresponding subsection of the patient monitoring worksheet; and
visually emphasize the corresponding subsection of the patient monitoring worksheet as incomplete.

6. The apparatus of claim 1, wherein the processor is further operable, when executing the medical information management application, to horizontally scroll tracked information for all of the display sections in response to touch-screen gesture control to permit display of different periods of time intervals.

7. The apparatus of claim 1, wherein the processor is further operable, when executing the medical information management application:
in a first mode of operation, to present a laboratory data display section having a column listing a plurality of laboratory data items and, for each of the laboratory data items, a row capable of tracking a value for the laboratory data item;
in a second mode of operation, to hide the laboratory data display section; and
to toggle between the first mode of operation and the second mode of operation in response to user input.

8. The apparatus of claim 1, wherein the plurality of drugs for the drugs display section, the plurality of fluids for the fluids display section, and the plurality of physiological data items are each defined by a corresponding template associated with a selected practice location.

9. A method for updating an electronic medical record of a patient, the method comprising:
retrieving, from a medical information management system, a patient monitoring worksheet displaying a subset of medical information relating to the delivery of medical care to a first patient, the medical information management system operable to maintain a plurality of patient monitoring worksheets;
presenting, on a display capable of receiving touch-responsive user input, the retrieved patient monitoring worksheet displaying medical information relating to the delivery of medical care to a patient, the patient monitoring worksheet having a maximum viewable time range selected from the range of thirty minutes to four hours and equally divided into a plurality of time intervals, and wherein the patient monitoring worksheet comprises a plurality of simultaneously viewable display sections comprising a drugs display section, a fluids display section, a vital signs display section, and a physiological data display section;
the drugs display section having a column listing a plurality of drugs and, for each of the drugs, a row capable of tracking of an amount of the drug administered for each of the time intervals, and wherein if a number of the drugs exceeds a drug list threshold, the drugs display section is vertically scrollable in response to touch-screen gesture control;
the fluids display section having a column listing of a plurality of fluids and, for each of the fluids, a row capable of tracking of an amount of the fluid administered or expelled for each of the time intervals, and wherein if a number of the fluids exceeds a fluid list threshold, the fluids display section is vertically scrollable in response to touch-screen gesture control;
the vital signs display section having a column indicating a scale and capable of tracking, for each of the equally distributed subintervals of time, a heart rate and a blood pressure of the patient charted on the scale; and
the physiological data display section having a column listing a plurality of physiological data items and, for each of the physiological data items, a row capable of tracking a value for the physiological data item for each of the time intervals, and wherein if a number of the physiological data items exceeds a physiological data item list limit, the physiological data display section is vertically scrollable in response to touch-screen gesture control;
wherein each of the time intervals of each of the display sections is a subsection;
determining, for each subsection, whether information tracked during that subsection is incomplete;

in a first mode of operation, permitting edit popups only for the ones of the subsections with incomplete information;

in a second mode of operation, permitting edit popups for any of the subsections, wherein toggling between the first mode of operation and the second mode of operation is based on user input;

detecting touch-screen input selecting a subsection with incomplete information; and presenting, in a portion of the display, an edit popup for the selected subsection, an edit popup permitting one or more of adding or editing of information tracked in the subsection, the information tracked in the subsection comprising one or more values;

determining, based on user input, one or more added or edited values of the edit popup;

updating the patient monitoring worksheet for the first patient by causing the one or more added or edited values to be stored by the medical information management system.

10. The method of claim 9, further comprising:
determining that a predefined time has passed after completion of a patient care associated with the patient monitoring worksheet;
determining one or more of the subsections having one or more of incomplete tracked information or an auto-populated value; and
communicating a notification indicating one or more of incomplete tracked information or an occurrence of an auto-populated value.

11. The method of claim 9, wherein the first value is determined based on one or more of an algorithm or a measure.

12. The method of claim 9, wherein the plurality of display sections further comprises an events display section, the method further comprising:
detecting a touch-screen input selection of a subsection of the events display section;
presenting in a portion of the display an events edit popup for the selected subsection of the events display section, the events edit popup permitting selection of an event to be tracked in the subsection;
transmitting the selected event and a corresponding timestamp to the central medical information management system; and
updating the subsection of the events display section with a visual indication of the entered event.

13. The method of claim 9, wherein the edit popup presents items trackable in the selected subsection, the method further comprising:
receiving a selection of a rapid entry indicator of one or more of the items trackable in the selected subsection;
determining that numeric values accompanying those items are required;
receiving a confirmation of the selected items without receiving numeric values for one or more of the selected items;
visually indicating each of the selected items in the corresponding subsection of the patient monitoring worksheet; and
visually emphasizing the corresponding subsection of the patient monitoring worksheet as incomplete.

14. The method of claim 9, further comprising horizontally scrolling tracked information for all of the display sections in response to touch-screen gesture control to permit display of different periods of time intervals.

15. The method of claim 9, further comprising:
in a first mode of operation, presenting a laboratory data display section having a column listing a plurality of laboratory data items and, for each of the laboratory data items, a row capable of tracking a value for the laboratory data item;
in a second mode of operation, hiding the laboratory data display section; and
toggling between the first mode of operation and the second mode of operation in response to user input.

16. The method of claim 9, the method further comprising:
identifying a first subsection configured to auto-populate a value;
upon determining a first value for the first subsection, auto-populating the first subsection with the first value;
presenting, in a portion of the display, an edit popup for the selected subsection, an edit popup permitting one or more of editing or verification of values for information tracked in the subsection;
determine, based on user input, an edited or verified value for the selected subsection; and
update the patient monitoring worksheet for the first patient by causing the edited or verified value to be stored by the medical information management system.

17. A system for updating an electronic medical record for a patient, the system comprising:
a central medical information management system operable to maintain a plurality of patient monitoring worksheets that correspond to patients associated with a medical practice at a practice location during a predetermined period of time;
one or more medical information management applications each residing on a wireless handheld device and operable, when executed, to:
present, on a display capable of receiving touch-responsive user input, a patient monitoring worksheet displaying a subset of medical information relating to the delivery of medical care to a first patient, the patient monitoring worksheet having a maximum viewable time range selected from the range of thirty minutes to four hours and equally divided into a plurality of time intervals, and wherein the patient monitoring worksheet comprises a plurality of simultaneously viewable display sections comprising a drugs display section, a fluids display section, a vital signs display section, and a physiological data display section;
the drugs display section having a column listing a plurality of drugs and, for each of the drugs, a row capable of tracking of an amount of the drug administered for each of the time intervals, and wherein if a number of the drugs exceeds a drug list threshold, the drugs display section is vertically scrollable in response to touch-screen gesture control;
the fluids display section having a column listing of a plurality of fluids and, for each of the fluids, a row capable of tracking of an amount of the fluid administered or expelled for each of the time intervals, and wherein if a number of the fluids exceeds a fluid list threshold, the fluids display section is vertically scrollable in response to touch-screen gesture control;
the vital signs display section having a column indicating a scale and capable of tracking, for each of the equally distributed subintervals of time, a heart rate and a blood pressure of the patient charted on the scale; and the physiological data display section having a column listing a plurality of physiological data items and, for each of the physiological data items, a row capable of tracking a value for the physiological data item for each of the time intervals, and wherein if a number of the physiological data items exceeds a physiological data item list limit, the physiological data display section is vertically scrollable in response to touch-screen gesture control;

wherein each of the time intervals of each of the display sections is a subsection;

detect a beginning of a new time interval;

identify a first subsection configured to auto-populate a value;

upon determining a first value for the first subsection, auto-populate the first subsection with the first value;

determine, for each subsection, whether information tracked during that subsection is incomplete;

in a first mode of operation, permit edit popups only for the ones of the subsections with incomplete information;

in a second mode of operation, permit edit popups for any of the subsections, wherein toggling between the first mode of operation and the second mode of operation is based on user input; and update the patient monitoring worksheet for the first patient by causing the first value to be stored by the medical information management system.

18. The system of claim 17, wherein the one or more medical information management applications operable when executed to:

determine that a predefined time has passed after completion of a patient care associated with the patient monitoring worksheet;

determine one or more of the subsections having one or more of incomplete tracked information or an auto-populated value; and communicate a notification indicating one or more of incomplete tracked information or an occurrence of an auto-populated value.

19. The system of claim 17, wherein the first value is determined based on one or more of an algorithm or a measure.

20. The system of claim 17, wherein the one or more medical information management applications operable when executed to present in a portion of the display an edit popup for a selected subsection, the edit popup permitting editing of values for information tracked in the subsection.

* * * * *